US011559072B2

(12) United States Patent
Leung et al.

(10) Patent No.: US 11,559,072 B2
(45) Date of Patent: *Jan. 24, 2023

(54) METHODS FOR PREPARING A COMESTIBLE MEAT PRODUCT

(71) Applicant: Upside Foods, Inc., Berkeley, CA (US)

(72) Inventors: Matthew Leung, Richmond, CA (US); Asha Godbole, Berkeley, CA (US); George C Engelmayr, Jr., Mountain View, CA (US); Nicholas J Genovese, Hayward, CA (US); Uma S Valeti, St. Paul, MN (US); Kathleen Carswell, San Francisco, CA (US)

(73) Assignee: Upside Foods, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/660,165

(22) Filed: Apr. 21, 2022

(65) Prior Publication Data

US 2022/0248727 A1 Aug. 11, 2022

Related U.S. Application Data

(63) Continuation of application No. 17/131,514, filed on Dec. 22, 2020, now Pat. No. 11,357,244, which is a continuation of application No. PCT/US2020/034949, filed on May 28, 2020.

(60) Provisional application No. 62/853,565, filed on May 28, 2019.

(51) Int. Cl.
*A23L 13/50* (2016.01)
*C12M 3/00* (2006.01)
*C12N 5/077* (2010.01)

(52) U.S. Cl.
CPC ............... *A23L 13/50* (2016.08); *C12M 3/00* (2013.01); *C12N 5/0658* (2013.01); *A23V 2002/00* (2013.01); *C12N 2513/00* (2013.01); *C12N 2535/10* (2013.01)

(58) Field of Classification Search
CPC ........ A23L 13/50; C12M 3/00; C12N 5/0658; C12N 2513/00; C12N 2535/10; A23V 2002/00
See application file for complete search history.

(56) References Cited

U.S. PATENT DOCUMENTS

| 5,786,215 | A | 7/1998 | Brown et al. |
|---|---|---|---|
| 6,835,390 | B1 | 12/2004 | Vein |
| 7,875,448 | B2 | 1/2011 | Furey |
| 8,294,632 | B2 | 10/2012 | Skarp |
| 9,023,642 | B2 | 5/2015 | Kleis et al. |
| 9,249,383 | B2 | 2/2016 | Yu et al. |
| 9,657,266 | B2 | 5/2017 | Kasuto et al. |
| 9,994,812 | B2 | 6/2018 | Kim et al. |
| 11,147,300 | B2 | 10/2021 | Leung et al. |
| 11,193,102 | B2 | 12/2021 | Ohkubo |
| 2005/0084958 | A1 | 4/2005 | Vein |
| 2005/0287660 | A1 | 12/2005 | Aubry et al. |
| 2007/0122901 | A1* | 5/2007 | Morita ................ C12N 5/0068 435/325 |
| 2008/0009063 | A1 | 1/2008 | Okano et al. |
| 2008/0208351 | A1 | 8/2008 | Besenbacher et al. |
| 2008/0293139 | A1 | 11/2008 | Watanabe |
| 2010/0184182 | A1 | 7/2010 | Hase |
| 2010/0216242 | A1 | 8/2010 | Shimizu et al. |
| 2011/0212493 | A1 | 9/2011 | Hirschel et al. |
| 2013/0029008 | A1* | 1/2013 | Forgacs ................ A23L 13/03 426/55 |
| 2013/0059339 | A1 | 3/2013 | Karerangabo et al. |
| 2014/0093618 | A1 | 4/2014 | Forgacs et al. |
| 2015/0125952 | A1 | 5/2015 | Kim et al. |
| 2016/0227830 | A1 | 8/2016 | Genovese et al. |
| 2016/0251625 | A1 | 9/2016 | Genovese et al. |
| 2017/0253849 | A1 | 9/2017 | Miller |

(Continued)

FOREIGN PATENT DOCUMENTS

| CN | 102232109 A | 11/2011 |
|---|---|---|
| CN | 108025112 A | 5/2018 |

(Continued)

OTHER PUBLICATIONS

Office Action as received in Mexican application MX/a/2022/006095 dated Jun. 1, 2022 [no English translation available].
Office Action as received in European application 20834000.0 dated Jun. 10, 2022.
Office Action as received in Chinese application 202080049214.1 dated Jul. 15, 2022 [no English translation available].
Datar et al., "Possibilities for an in vitro meat production system," Innovative Food Science and Emerging Technologies, vol. 11, No. 1, Jan. 1, 2010, pp. 13-22.

(Continued)

*Primary Examiner* — Titilayo Moloye
(74) *Attorney, Agent, or Firm* — Keller Preece PLLC

(57) ABSTRACT

The substrates, systems, and methods described herein relate to textured substrates for preparing a comestible meat product. Substrates and methods are described herein for controlling one or more of growth, adhesion, retention, and/or release of cells (e.g., of a cell sheet) on or from the surface of the substrate. A method of preparing a comestible meat product may include applying a plurality of non-human cells to at least one patterned texture substrate, growing the cells on the patterned texture substrate to form the comestible meat product, and separating the comestible meat product from the patterned texture substrate. The patterned texture allows for improved growth, adhesion, retention, and/or release of cells as compared to another surface not comprising the patterned texture. In some embodiments, the cell culture substrate surfaces include a plurality of regions corresponding to a plurality of patterned textures.

20 Claims, 26 Drawing Sheets

(56) References Cited

U.S. PATENT DOCUMENTS

| | | |
|---|---|---|
| 2019/0024079 A1 | 1/2019 | Genovese et al. |
| 2020/0165569 A1 | 5/2020 | Genovese et al. |
| 2021/0106032 A1 | 4/2021 | Leung et al. |
| 2021/0145031 A1 | 5/2021 | Leung et al. |
| 2021/0171912 A1 | 6/2021 | Genovese et al. |

FOREIGN PATENT DOCUMENTS

| | | |
|---|---|---|
| EP | 2 736 357 B1 | 6/2014 |
| KR | 10-2014-0040212 A | 4/2014 |
| KR | 10-2018-0026792 A | 3/2018 |
| KR | 0026792 A | 3/2018 |
| WO | WO 99/31222 | 6/1999 |
| WO | WO 2006/041429 A2 | 4/2006 |
| WO | WO 2014/036187 A1 | 3/2014 |
| WO | WO 2018/011805 A2 | 1/2018 |
| WO | WO 2019/014652 A1 | 1/2019 |
| WO | WO 2019/122239 A1 | 6/2019 |
| WO | WO 2020/243324 A1 | 12/2020 |

OTHER PUBLICATIONS

Gaydhane et al., "Cultured meat: state of the art and future," Biomanufacturing Reviews, vol. 3, No. 1, Mar. 19, 2018.
U.S. Appl. No. 17/131,514, Mar. 3, 2021, Office Action.
U.S. Appl. No. 17/131,514, Jun. 16, 2021, Office Action.
U.S. Appl. No. 17/131,514, Dec. 6, 2021, Office Action.
U.S. Appl. No. 17/131,514, Mar. 29, 2022, Notice of Allowance.
U.S. Appl. No. 17/100,705, Apr. 21, 2021, Office Action.
U.S. Appl. No. 17/100,705, Aug. 10, 2021, Notice of Allowance.
U.S. Appl. No. 17/469,687, Apr. 13, 2022, Notice of Allowance.
U.S. Appl. No. 17/469,680, Apr. 15, 2022, Office Action.
U.S. Appl. No. 17/469,680, Jul. 15, 2022, Notice of Allowance.
U.S. Appl. No. 17/660,170, Jul. 21, 2022, Office Action.
International Search Report and Written Opinion dated Nov. 9, 2020, in International Application No. PCT/US2020/034949, 15 pages.
International Search Report and Written Opinion dated Mar. 12, 2021, in International Application No. PCT/US2020/061676, 13 pages.
Acevedo et al., "Micropatterning Technology to Design an Edible Film for In Vitro Meat Production", Food and Bioprocess Technology, vol. 11, No. 7, Mar. 25, 2018, pp. 1267-1273.
Bhat et al., Prospectus of cultured meat-advancing meat alternatives, Journal of Food Science and Technology, vol. 48, no. 2, Dec. 30, 2010, pp. 125-140.
Brunette, "Fibroblasts on micromachined substrata orient hierarchically to grooves of different dimensions," Exp Cell Res. 1986; 164(1):11-26.
Brunette, "Spreading and orientation of epithelial cells on grooved substrata," Exp Cell Res. 1986; 167(1):203-217.
Clark et al., "Topographical control of cell behaviour: II. multiple grooved substrata," Development 108, 635-644 (1990).
Datar et al., "Possibilities for an in vitro meat production system," Innovative Food Science and Emerging Technologies, vol. 11, no. 1, 1 Jan. 2010, pp. 13-22.
Gaydhane et al., "Cultured meat: state of the art and future," Biomanufacturing Reviews, vol. 3, No. 1, 19 Mar. 2018.
Karuri et al., "Biological length scale topography enhances cell-substratum adhesion of. human corneal epithelial cells," J Cell Sci. 2004; 117: 3153-3164.
Lam et al., "Microfeature guided skeletal muscle tissue engineering for highly organized 3-dimensional free-standing constructs", Biomaterials, vol. 30, No. 6, Feb. 1, 2009, pp. 1150-1155.
Ostrovidov et al., "Skeletal Muscle Tissue Engineering: Methods to Form Skeletal Myotubes and Their Applications" Tissue Engineering: Part B, vol. 20, No. 5, Oct. 1, 2014 (Oct. 1, 2014), pp. 403-436.
Riboldi et al., "Electrospun degradable polyesterurethane membranes: potential scaffolds for skeletal muscle tissue engineering," Biomaterials, vol. 26, No. 22, Aug. 1, 2005, pp. 4606-4615.
Hosseini et al. "Engineered contractile skeletal muscle tissue on a microgrooved methacrylated gelatin substrate." Tissue Eng Part A. Dec. 2012;18(23-24):2453-65. (Year: 2012).
Bajaj et al. "Patterning the differentiation of C2C12 skeletal nnyoblasts. "Integrative Biology, vol. 3, Issue 9, Sep. 2011, pp. 897-909 (Year: 2011).
Cha et al. "Study of myoblast differentiation using multi-dimensional scaffolds consisting of nano and micropatterns. "Biomater Res . Jan. 11, 2017;21:1. (Year: 2017).
Charest et al. "Myoblast alignment and differentiation on cell culture substrates with microscale topography and model chemistries." Biomaterials. Apr. 2007;28(13):2202-10. (Year: 2007).
Zeng et al. "A minimally invasive method for retrieving single adherent cells of different types from cultures"Sci Rep. Jun. 24, 2014;4:5424. (Year: 2014).
Willem Visser et al. "Quantifying Cell Adhesion through Impingement of a Controlled Microjet."Biophys J. Jan. 6, 2015; 108(1): 23-31.(Year: 2015).
"What is Fluid Mechanics." Mechanical Engineering. Penn State College of Egineering. Retrieved on Dec. 1, 2021. Retrieved from https://www.rne.psu.eduicinnbala/Learning/Fluid/Introductory/what is fluid rnechanics.htm (Year: 2021).
Office Action as received in European application 20745342.4 dated Dec. 9, 2021.
Examination Report as received in Australian application 2020284005 dated May 2, 2022.
Office Action as received in Canadian application 3,141,870 dated Jun. 3, 2022.
Office Action as received in Israeli application 288338 dated May 25, 2022.
U.S. Appl. No. 17/131,514, dated Mar. 3, 2021, Office Action.
U.S. Appl. No. 17/131,514, dated Jun. 16, 2021, Office Action.
U.S. Appl. No. 17/131,514, dated Dec. 6, 2021, Office Action.
U.S. Appl. No. 17/131,514, dated Mar. 29, 2022, Notice of Allowance.
U.S. Appl. No. 17/100,705, dated Apr. 21, 2021, Office Action.
U.S. Appl. No. 17/100,705, dated Aug. 10, 2021, Notice of Allowance.
U.S. Appl. No. 17/469,687, dated Apr. 13, 2022, Notice of Allowance.
U.S. Appl. No. 17/469,680, dated Apr. 15, 2022, Office Action.
Examination Report as received in Australian application 2022241490 dated Nov. 3, 2022.
Office Action as received in Korean application 10-2022-7015187 dated Nov. 1, 2022.
Office Action as received in Canadian application 3,160,109 dated Sep. 15, 2022.
Office Action as received in Japanese application 2022-525657 dated Oct. 31, 2022 [no English translation available].
U.S. Appl. No. 17/812,315, dated Oct. 31, 2022, Office Action.
U.S. Appl. No. 16/7660,170, dated Nov. 8, 2022, Notice of Allowance.

* cited by examiner

Die-Cut Patterned Texture 800 grit Patterned Texture

Laser Engraved Patterned Texture

Cross-hatched Patterned Texture

Linear and Spot Patterned Texture

METHODS FOR PREPARING A COMESTIBLE MEAT PRODUCT

CROSS-REFERENCE TO RELATED APPLICATIONS

This application is a continuation of U.S. patent application Ser. No. 17/131,514, filed on Dec. 22, 2020, which is a continuation of PCT Application No. PCT/US2020/034949, filed on May 28, 2020, which claims the benefit of and priority to U.S. Provisional Patent Application No. 62/853,565, filed on May 28, 2019. Each of the aforementioned applications is hereby incorporated by reference in its entirety.

BACKGROUND

Cell culture substrates are used to support attachment, proliferation, and differentiation of cells. In some tissue engineering applications, cell culture substrates include substantially three-dimensional substrates (e.g., scaffolds) and/or substantially two-dimensional substrates (e.g., petri dish) configured to support the formation of single and multilayered cellular sheets. However, there remains a need for substrates that allow for improved characteristics of growth, retention, adhesion, and/or release of cell sheets. For example, there is a need to reduce premature cell sheet detachment from a substrate. Therefore, additional substrates, systems, and methods of manufacturing substrates for culturing cells and forming single and multilayered cellular sheets are desirable

SUMMARY

Described here are comestible meat product substrates, methods of preparing a comestible meat product, and methods of manufacturing thereof. Generally, the apparatuses, systems, and methods described herein use a substrate for growing a comestible meat product. In general, these methods include the step of applying a plurality of non-human cells to at least one patterned texture substrate, growing the non-human cells on the patterned texture substrate to form the comestible meat product, and separating the comestible meat product from the patterned texture substrate. The comestible meat product may comprise a cell sheet.

In some embodiments, the plurality of non-human cells may be applied without a non-naturally secreted exogenous scaffold. In some embodiments, the cell sheet may be held intact by an extracellular matrix secreted by the cells. In some embodiments, separating the comestible meat product from the patterned comprises separating the cell sheet from the patterned texture substrate. In some embodiments, the comestible meat product may be separated contemporaneously from the patterned texture substrate. In some embodiments, separating the comestible meat product from the patterned texture substrate may comprise inducing one or more of cellular contraction, cellular relaxation, and mechanical detachment.

In some embodiments, the method may further include arranging a plurality of the patterned texture substrates in a three-dimensional lattice. In some embodiments, the method may further include disposing the at least one patterned texture substrate in a bioreactor. In some embodiments, the method may further include positioning a first patterned textured substrate adjacent a second patterned textured substrate and delivering cell culture medium between the first and second patterned texture.

In some embodiments, the comestible meat product comprises a volume between about 0.0001 $m^3$ and about 0.1 $m^3$. In some embodiments, the plurality of non-human cells are applied for at least 7 days. In some embodiments, the plurality of non-human cells are applied for at least 14 days. In some embodiments, growing the cells on the patterned texture substrate promotes cell alignment based on the patterned texture substrate. In some embodiments, the cells may comprise one or more cells from livestock, poultry, game, and aquatic animal species. In some embodiments, the cells may comprise one or more cells from at least one of a vertebrate and invertebrate species. In some embodiments, the cells may comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pluripotent cells, somatic stem cells, and endothelial cells.

In some embodiments, the patterned texture substrate may comprise a plurality of channels each having a depth of between about 0.01 μm and about 100 μm and a width of between about 1 μm and about 5 mm, wherein adjacent channels are separated from each other by at least about 5 μm. In some embodiments, the patterned texture substrate may be substantially planar.

In some embodiments, a substrate for growing a comestible meat product may comprise a surface comprising at least one patterned texture, wherein the at least one patterned texture is configured to promote one or more of: growth of the comestible meat product on the substrate, adhesion of the comestible meat product on the substrate, retention of the comestible meat product on the substrate, and release of the comestible meat product from the substrate. The comestible meat product may comprise an intact cell sheet.

In some embodiments, the substrate may comprise a plurality of regions where each region of the substrate may comprise at least one of the patterned textures. In some embodiments, two or more regions comprise the same patterned texture. In some embodiments, the substrate may comprise a thickness of between about 10 μm and about 10 cm. In some embodiments, the substrate may comprise a solid material or a semi-solid material.

In some embodiments, a set of the plurality of regions may be arranged periodically. In some embodiments, a set of the plurality of regions may be arranged non-periodically. In some embodiments, the substrate may define a substrate dimension and the at least one patterned texture defines a surface dimension, and a ratio of the surface dimension to the substrate dimension may be between about 0.0001:1 and about 0.1:1. In some embodiments, the patterned texture may have a predetermined direction. In some embodiments, the predetermined direction may comprise one or more of a radial, circular, non-linear, spot, and cross-hatched pattern. In some embodiments, the patterned texture may comprise one or more channels, recesses, and protrusions.

In some embodiments, the patterned texture may comprise a plurality of channels each having a depth of between about 0.01 μm and about 100 μm and a width of between about 1 μm and about 5 mm. Adjacent channels may be separated from each other by at least about 5 μm.

Also described herein are cell culture substrates, methods of culturing cells using the cell culture substrates, and methods of manufacturing thereof. Generally, the apparatuses, systems, and methods described herein use a cell culture substrate to grow and adhere a population of cells to a surface of the substrate. A surface of a cell culture substrate includes at least one patterned texture that allows for one or more of improved growth, adhesion, and retention of cells on the substrate, and/or improved release of cells from the substrate as compared to a surface not comprising the patterned texture.

In some embodiments, a surface of a cell culture substrate may include a plurality of regions where each region has a patterned texture. In some of these embodiments, two or more of the regions have the same patterned texture. In some of these embodiments, a set of the plurality of regions are arranged periodically. In some of these embodiments, a set of the plurality of regions are arranged non-periodically.

In some embodiments, the cells are held together by an extracellular matrix secreted by the cells to form a cell sheet. In some embodiments, the cells are in a cell sheet. In some embodiments, the surface not comprising the patterned texture is absent surface modification. In some embodiments, the patterned texture comprises a plurality of surface characteristics. In some embodiments, the substrate defines a substrate dimension and the at least one patterned texture defines a surface dimension, and a ratio of the surface dimension to the substrate dimension is between about 0.0001:1 and about 0.1:1. In some of these embodiments, the at least one patterned texture comprises a set of linear channels in parallel to each other.

In some embodiments, the patterned texture has a predetermined direction. In some embodiments, the predetermined direction comprises one or more of a radial, circular, non-linear, spot, and cross-hatched pattern. In some embodiments, the patterned texture has a random spatial distribution pattern.

In some embodiments, the substrate allows for intact and/or contemporaneous release of the cell sheet from the substrate. In some embodiments, the substrate inhibits release of the cell sheet from the substrate.

In some embodiments, the patterned texture comprises one or more channels, recesses, and protrusions. In some embodiments, the patterned texture comprises a plurality of channels each having a depth of between about 0.01 µm and about 100 µm and a width of between about 1 µm and about 5 mm, wherein adjacent channels are separated from each other by at least about 5 µm. In some embodiments, the substrate is composed of a solid material or a semi-solid material. In some embodiments, the substrate has a thickness of between about 10 µm and about 10 cm.

In some embodiments, the substrate is arranged adjacent to at least one other cell culture substrate. In some embodiments, a plurality of substrates are arranged in a three-dimensional lattice. In some embodiments, the substrate is placed into and/or integral with a culture vessel, wherein the culture vessel is selected from one or more of a bioreactor, well, petri dish, plate, flask, bottle, tank, box, and fixed surface. In some embodiments, the cells comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pericytes, pluripotent stem cells, somatic stem cells, and endothelial cells. In some embodiments, the cells comprise one or more cells from human, primate, livestock, poultry, game, and aquatic animal species. In some embodiments, the cells comprise one or more cells from vertebrate and invertebrate species.

In some embodiments, the surface is substantially planar. In some embodiments, the surface is not planar, e.g. a roller bottle. In some embodiments, the substrate does not comprise a non-naturally secreted exogenous scaffold.

Also described here are methods for improving one or more of growth, adhesion, and retention of cells on a cell culture substrate, and/or improved release of cells from the substrate. In general, these methods include the step of contacting a population of cells to the cell culture substrate.

In some embodiments, the method includes detaching the cells from the substrate as a cell sheet. In some embodiments, the method includes detaching the cells from the substrate in a set of predetermined sections. In some embodiments, the method includes detaching the cells from the substrate, resulting in a plurality of randomly generated/randomly sized sections. In some embodiments, the method includes detaching the cells as a cell sheet comprises inducing one or more of cellular contraction, cellular relaxation, and mechanical detachment.

In some embodiments, the method includes arranging a plurality of cell culture substrates in a parallel plate configuration. In some embodiments, the method includes delivering cell culture media between adjacent cell culture substrates. In some embodiments, the method includes delivering cell culture media to a surface of the substrate. In some embodiments, a flow of the cell culture media delivered to the substrate is aligned to the at least one patterned texture. In some embodiments, the method includes forming one or more patterned textures on a cell culture substrate, wherein the substrate comprises a plurality of regions corresponding to the one or more patterned textures.

In some embodiments, the method includes forming the one or more of patterned textures wherein such method comprises one or more of additive and subtractive manufacturing techniques. In some embodiments, the method includes forming the plurality of patterned textures comprises one or more of machining, cutting, milling, abrasion, etching, engraving, embossing, scratching, scoring, casting, water discharge, chemical etching, laser ablation, electron beam lithography, sputter coating, vapor-phase deposition, printing, adhesive bonding, and welding. In some embodiments, the method includes arranging the plurality of regions periodically.

In some embodiments, the method includes arranging the plurality of regions non-periodically. In some embodiments, the substrate is placed in a culture vessel. In some embodiments, the substrate is arranged adjacent to at least one other cell culture substrate. In some embodiments, a plurality of the substrates are arranged in a three-dimensional lattice. In some embodiments, the substrate is used in one or more tissue engineering, biomedical, oncology, textile, diagnostic, therapeutic, synthetic biology, bioremediation, energy storage, and biosensor applications. In some embodiments, a biocompatible coating is applied over a surface of the substrate.

Also described here are methods of generating a cell sheet comprising a comestible tissue product. In general, these methods include the step of culturing cells on any one of the substrates described herein, where the cells are grown without an exogenously provided scaffold.

Also described here are methods of generating a cell sheet comprising a comestible tissue product. In general, these methods include the step of culturing cells (e.g. self-renewing cells, e.g. differentiated cells) on any of the substrates described herein, where the cells are derived from vertebrate, invertebrate, human, primate livestock, poultry, game, and aquatic animal species. The cells are grown without an exogenously provided scaffold. In some embodiments, any of the substrates described herein may be composed of a ceramic. In some embodiments, any of the substrates described herein may be configured for growing a comestible meat product.

DETAILED DESCRIPTION

I. Substrates

Substrates Comprising Patterned Textures

Figure 1A:
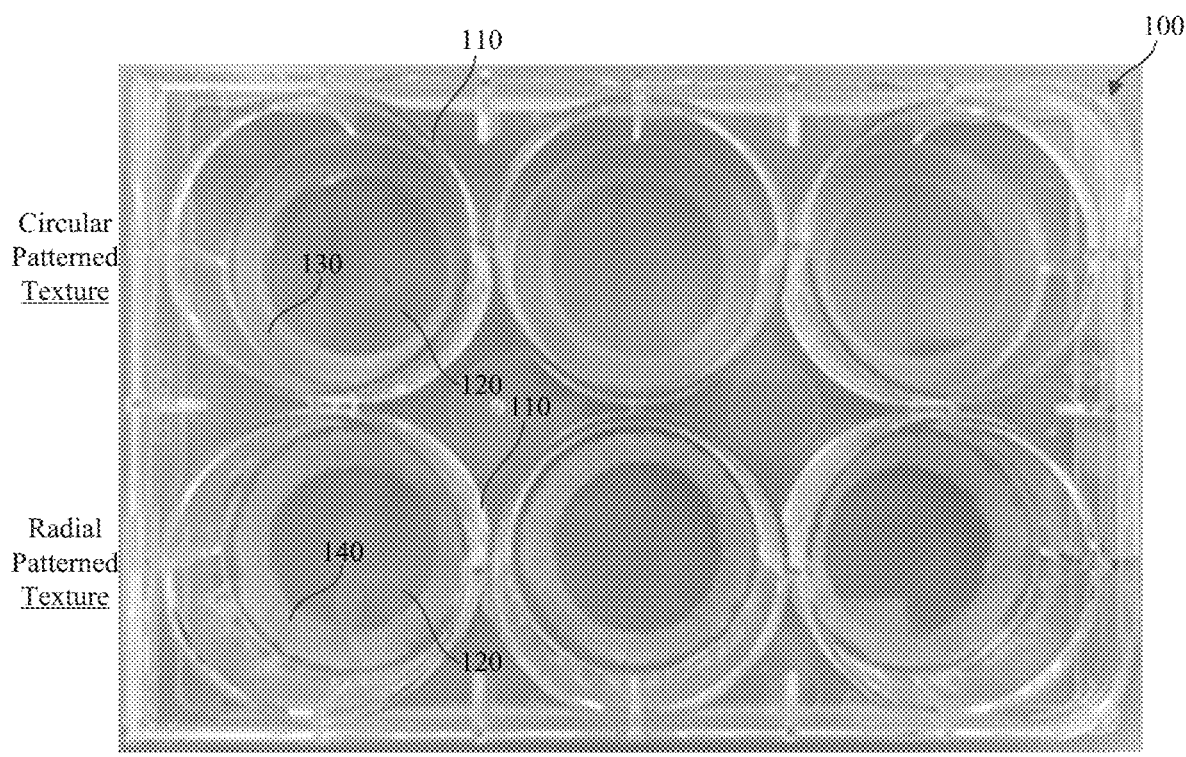
FIGS. 1A-1B are illustrative views of exemplary embodiments of a set of cell culture substrates placed in a corresponding set of wells.

The cell culture substrates comprising patterned textures, systems, and methods provided herein are useful to control the characteristics of growth, adhesion, release and/or retention of cells (e.g., cell sheets) grown on a surface of a cell culture substrate. The cell culture substrates described herein allow for control of one or more of cell (e.g., cell sheet) growth, adhesion, retention, and release (e.g., detachment) using at least one patterned texture on a surface of the substrate. As used herein, a "texture" refers to a set of surface characteristics (e.g., physical properties, surface features, patterns) of a cell culture substrate. In some embodiments, the cell culture substrates described herein may be used to grow a comestible meat product.

As used herein, a "patterned texture" refers to a predetermined/planned set of surface characteristics (e.g., physical properties, surface features, patterns) that are introduced into (e.g., formed, added, subtracted) the surface of a cell culture substrate. The patterned texture(s) are generally introduced into an otherwise, non-patterned surface of a substrate; a non-patterned surface of a substrate (also interchangeably referred to herein as a surface of a substrate not comprising a patterned texture) is generally the cell culture substrate, absent any additional processing steps and surface modifications post-substrate formation (e.g., it is the cell culture substrate "as is" without any additional surface characteristics/patterned textures introduced into it). As provided herein, a cell substrate is modified using one or more manufacturing techniques described herein, to form a surface having a patterned texture over one or more regions of the substrate.

In some embodiments, the growth, adhesion, retention, and/or release of cells on the cell culture substrates described herein are improved over non-patterned textured cell culture substrates. Without being limited to any theory or mechanism, the surface of the cell substrate having a patterned texture surface can mechanically interact with a population of cells and allow for growth and control retention of a single and/or multi-layered cell sheet (e.g., tissue) on the substrate for a predetermined (e.g., controlled, reduced, extended) amount of time. That is, the patterned texture surface and cell sheets can mechanically interact to retain the cell sheet to the substrate as the cells (e.g., cell sheets) grow and develop over time. This may allow for the growth and release of a comestible meat product having, for example, a texture and consistency similar to a naturally produced meat product (e.g., one that involves the slaughter of an animal).

The parameters of the patterned textures of the disclosure may be based on the cell type, desired growth characteristics, and timing of release from the substrate. Patterned textures may be particularly effective in cell sheet retention based on cell phenotype.

As a result of one or more patterned textures, the substrate may be used to control retention of a cell sheet to the surface of the substrate. Likewise, the patterned texture for a given cell type may inhibit premature detachment of one or more regions of a cell sheet to allow for prolonged culture and maturation of cells. This allows, in some embodiments, a substantially whole cell sheet to be released at a predetermined (e.g., controlled, reduced, extended) time (e.g., with substantially little cell sheet remaining attached to the substrate or broken off). Additionally or alternatively, the cell sheet may be detached in a set of separable sections. For example, the patterned texture is configured to allow a cell sheet grown on a cell culture substrate to be detached in a plurality of sections (e.g., 2 or more pieces).

By contrast, some cell sheets grown on conventional planar cell culture substrates prematurely release from the cell substrate, resulting in aborted operations and suboptimal yields. For example, cell sheets grown on conventional planar cell culture substrates may not allow for release of the cell sheet having a texture and consistency similar to naturally produced meat.

In some embodiments, premature cell detachment from a cell culture substrate is prevented in applications such as tissue engineering of contractible cells. Although the substrates are suitable for any culture vessel, cell type, and application, some embodiments of the cell substrates described herein are used for tissue engineering of comestible tissue (e.g., meat product) where an entirely cell-derived, native-like product may be desirable. The cell substrates provided herein include a surface having one or more patterned textures sufficient for growth, adhesion, and retention of cells to the substrate for a predetermined amount of time.

Generally, the substrates, systems, and methods described herein use a cell culture substrate to grow and adhere a population of cells to a surface of the substrate for at least a predetermined amount of time. The cell culture substrate has a surface including at least one patterned texture that allows for improved growth, adhesion, and retention of cells on the substrate, and/or improved release of cells from the substrate as compared to a surface not comprising the patterned texture. In some embodiments, the patterned texture of the surface is used to scale cell sheet growth to a desired size (e.g., as part of a commercial-scale process, to form comestible tissue such as a meat product).

Characteristics of a patterned texture include one or more of a feature, shape, directionality, dimensions (e.g., length, width, depth, thickness, curvature, volume, area), density, periodicity, surface roughness, porosity, material, and the like. As used herein, the term "patterned" includes one or more instances of a surface characteristic and is not limited to a repeating characteristic or configuration. In an exemplary embodiment, a patterned texture of a surface may include a set of linear grooves extending radially from a center of a substrate to the edges of the substrate.

The characteristics of a patterned texture are selected based on the cell type, and desired growth, retention, and release characteristics of the cells on the substrate (e.g. the growth, retention, and release characteristics of a cell sheet formed on the substrate). As used herein, a cell sheet refers interchangeably to a mono-layer of cells or a multi-layer set of cells and/or exogenous extracellular matrix (ECM) protein grown on a cell culture substrate. In some embodiments, a cell sheet is held intact by an ECM generated by the cells and/or cells may form a sheet via cell-to-cell binding proteins to form a substantially continuous unit. For example, the secretion of sufficient ECM proteins can allow constituent cells to stick together as a substantially continuous cell sheet via a combination of cell-cell and cell-ECM interactions. In some embodiments, a cell sheet is held intact by an endogenously produced scaffold such as an ECM.

Exemplary embodiments of the present disclosure are directed toward textured cell culture substrates, systems, and methods for use in a variety of applications and are not particularly limited. They may be used in one or more tissue engineering (e.g. for therapeutic purposes, e.g. for comestible food production), biomedical, oncology, textile (e.g., clothing, upholstery), diagnostic, therapeutic, synthetic biology, bioremediation, energy storage, and biosensor applications. For example, synthetic biology includes use of cell biology to synthesize a product distinct from the cells themselves (e.g., biofuel production, proteins or polysaccharides for textiles). Bioremediation may in some embodiments utilize cells to sequester an undesired substrate and/or convert the substrate into a benign form. A biosensor may use cellular responses to measure a stimulus and generate an output signal.

Cell growth for tissue engineering applications such as comestible tissue production faces particular challenges, addressed by the cell culture substrates, systems, and methods provided herein. For example, in some embodiments, growth of a cell sheet on a cell culture substrate requires sufficient time where the cells remain adhered to the substrate for a predetermined time period (e.g., growth period) and/or cell state (e.g., observed metabolic signature or cell differentiation change). But, once the cells are grown, then it is optimal that the cell sheets are released in predetermined dimensions and in a substantially intact and/or contemporaneous manner.

Conventional cell culture substrates providing smooth surfaces for cell growth generally provide inferior tissue retention characteristics (e.g., retention time) as compared to the patterned texture surfaces described herein. Conventional cell culture substrates used for biomedical applications may frequently include surface coatings to promote cell sheet adherence and growth. However, these solutions are inadequate for comestible tissue production as the coatings are costly and short-lived such that they may degrade and contaminate the comestible tissue product. By contrast, the textured cell culture substrates as described herein may be cost-effectively scaled to grow cells (e.g., cell sheets or tissue) of sufficient dimensions (e.g., cell sheets) to form comestible tissue. Thus, the cell culture substrates described herein provide significant improvements to one or more of growth, adhesion, and retention of cells on the substrate over conventional techniques.

In some embodiments, the patterned texture of the surface is useful in scaling cell sheet growth to any desired size, which may improve the aesthetics and acceptance of tissue engineered products for the intended applications, such as a comestible tissue product. Conventional techniques using coatings and/or conjugated peptides for cell adherence and retention are less suitable for large-scale manufacture of comestible tissue and other tissue engineered products due to expense of non-durable coating reagents. By contrast, the methods and systems described herein can be used to generate cell sheets of any size desired. In some embodiments, the methods and systems are used to generate cell sheets larger those produced using known methods.

A surface of a cell culture substrate may include a plurality of regions corresponding to a plurality of patterned textures. For example, the arrangement of these plurality of patterned textures are useful for growing and releasing continuous, unbroken multi-layered cell sheets that are detached from a substrate without significant separation of tissue. In some embodiments, growth of tissue of a predetermined size and shape is controlled based on one or more factors including but not limited to the arrangement of patterned textures, a ratio of a patterned texture surface to the non-patterned texture surface, periodicity of the patterned texture, and the like.

The cell culture substrates described herein aid retention of non-contractile cell types and are particularly useful for retention of contractile cell types to a cell culture substrate.

Contractile cell types (e.g., muscle-derived cells) such as myoblasts have been conventionally challenging to retain on cell substrates for extended periods of time. Retention of such contractile cell types may be improved using the patterned textured substrates described herein.

As used herein, the characteristics of the substrate as a whole are independent of the characteristics of its surface (surface characteristics) due to the patterned texture applied to the surface of the substrate. For example, the cell culture substrates described herein may have a shape that may generally be described as substantially planar (e.g., flat) or curved. However, a local region of the surface of the cell culture substrate has surface characteristics having a patterned texture comprising a predetermined arrangement of one or more of channels, recesses, protrusions, ridges, grooves, scratches, edges, indentations, blind holes, hills-and-valleys, undercuts, threading (e.g., tapped thread) combinations thereof, and the like that may not match the overall characteristics of the substrate.

Substrate dimensions are specific to the dimensions of the substrate itself (e.g., relative to the substrate, thickness of the substrate) while surface dimensions are dimensions relative to the surface of the substrate (e.g., depth of a groove in the surface). That is, a substrate has macro-level dimensions (e.g., substrate dimensions) that differ from micro-level dimensions (e.g., surface dimensions) of its substrate surface. A dimension such as a substrate dimension and a surface dimension refers to a magnitude in at least one direction including, but not limited to, length, width, depth, thickness, curvature, volume, area, and the like.

The cell culture substrate is characterized by one or more substrate dimensions including one or more of thickness, depth, width, length, diameter, curvature, volume, and area of the substrate. Similarly, the patterned texture of the surface is characterized by one or more surface dimensions including one or more of thickness, depth, width, length, diameter, curvature, volume, and area of the surface. In some embodiments, the patterned texture can comprise a plurality of channels each having a depth of between about 0.01 μm and about 100 μm, and a width of between about 1 μm and about 5 mm; adjacent channels are separated from each other by between about 5 μm and about 3 cm. For example, the plurality of channels may comprise a depth of between about 0.1 μm and about 100 μm, between about 1 μm and about 50 μm, and between about 20 μm and about 80 μm, including all values and sub-ranges in-between. The plurality of channels may comprise a width between about 1 μm and about 5 mm, between about 1 μm and about 3 mm, between about 1 μm and about 2 mm, and between about 1 μm and about 1 mm, including all values and sub-ranges in-between. Adjacent channels may be separated from each other by between about 25 μm and about 100 μm, between about 100 μm and about 500 μm, between about 5 μm and about 500 μm, and between about 500 μm and about 3 cm, including all values and sub-ranges in-between. The cell culture substrates comprise a thickness of at least about 10 μm. In some embodiments, a cell culture substrate has a thickness of between about 10 μm and about 20 cm, including all values and sub-ranges in-between. In some embodiments, the plurality of channels may each extend along a surface of the substrate.

Generally disclosed herein are cell culture substrates comprising a surface comprising at least one patterned texture that allows for one or more of improved growth, adhesion, and retention of cells on the substrate, and/or improved release of cells from the substrate as compared to a surface not comprising the patterned texture. Generally, the patterned texture comprises one or more channels, recesses, protrusions, ridges, grooves, scratches, edges, indentations, blind holes, hills-and-valleys, undercuts. Furthermore, each patterned texture feature on a surface may have one or more sub-textures. The substrate having a patterned texture surface may inhibit release of the cells (e.g., cell sheet) from the substrate for a predetermined amount of time. Conversely, the substrate having a patterned texture surface allows for intact and/or contemporaneous release of cells (e.g., cell sheet) from the substrate at a predetermined time and/or cell state. For example, the release is controlled to reduce or extend for a predetermined time and/or cell state relative to a non-patterned texture surface. As used herein, a non-patterned texture surface, such as a conventional cell culture substrate, does not undergo additional surface processing steps and surface modifications after formation of the substrate. Accordingly, cells grown on the patterned texture surface of a substrate may form a cell sheet having a predictable and consistent shape and size due to the adhesion and retention of the cells to the patterned texture. For example, cells may grow into one or more of the channels, recess, and protrusions of the patterned texture. Furthermore, release of the cell sheet may be spontaneous or aided by one or more mechanical, fluidic (e.g., fluid-based shear stress), chemical, optical, thermal, and electrical release mechanisms.

The cell culture substrates described herein can be composed of one or more of a solid material and a semi-solid material (e.g., hydrogel). In some embodiments, the substrate is substantially non-degradable. In some embodiments, a cell culture substrate is composed of a material including, but not limited to, one or more of polychlorotrifluoroethylene, polyetherimide, polysulfone, polystyrene, polycarbonate, polypropylene, silicone, polyetheretherketone, polymethylmethacrylate, nylon, acrylic, polyvinylchloride, vinyl, phenolic resin, petroleum-derived polymers, glass, polyethylene, terephthalate, stainless steel, titanium, aluminum, cobalt-chromium, chrome, silicates, glass, alloys, ceramics, carbohydrate polymer, mineraloid matter, and combinations or composites thereof. In some embodiments, each material or layer of the cell culture substrate may comprise a corresponding patterned texture surface comprising predetermined cell adhesion and tissue retention properties. This may aid the manufacture and allow for economical and scalable production of the cell culture substrates described herein.

The cell culture substrates described herein may be sized and shaped to be placed into and/or integral with any suitable culture vessel including, but not limited to, one or more of a bioreactor, well, petri dish, plate, flask, bottle, tank, box, and fixed surface. In some embodiments, a set of cell culture substrates are used in a predetermined arrangement. For example, the cell substrate may be a thin, circular disk sized for a corresponding adherent cell culture vessel (e.g., well). In other of these embodiments, the set of substrates are arranged in a parallel plate configuration (e.g., adjacent to each other) that allow multi-layered cell sheets to be formed in a culture vessel. For example, the parallel plate configuration allows for cell culture media (e.g., growth media, nutrients) perfusion between the plates. For example, a set of planar substrates can be separated by a gap through which fluid media is perfused such that cells are grown on the set of substrates. In some embodiments, cell culture media may be delivered to a surface of the substrate.

In some embodiments, cell culture substrates do not include an exogenous non-naturally secreted scaffold structure and the cells/cell sheets are grown in the absence of an exogenous non-naturally secreted scaffold structure (but can be grown in the presence of a naturally secreted endogenously produced ECM for example). Accordingly, in some embodiments the cell culture substrates and corresponding patterned texture surface may be scaffold-less (e.g., exclude three-dimensional, porous and/or lattice-like structures that are not endogenously generated). In other embodiments, the cell culture substrates are arranged in and/or are in conjunction with a three-dimensional lattice-like configuration that is exogenously provided (e.g., scaffold).

A patterned texture of a substrate may enable generation of a comestible meat product having one or more predetermined tissue characteristics (e.g., size, consistency, texture). For example, linear channels may facilitate growth of tubular like tissue structures similar to avian tissue (e.g., poultry fibers). Net or dot like structures may facilitate growth of a tissue texture similar to aquatic animal tissue (e.g., fish). In some embodiments, the patterned texture may be configured to facilitate tissue separation and/or processing of the comestible meat product.

In some embodiments, the patterned textures of the disclosure comprise at least one predetermined direction that characterizes the pattern applied to the cell culture substrate. Such a patterned texture has a direction and shape comprising one or more of circumferential, radial, cross-hatched, random, linear, curved, spiral (e.g., Fibonacci spiral), ovoid, ellipsoid, sinusoidal, polygonal, tessellated (e.g., Voronoi tessellation), non-linear (e.g., zigzag), fish scale like (e.g., ctenoid, cycloid, placoid, ganoid) combinations thereof, and the like. As used herein, a pattern having a direction comprises a line that is one or more of continuous, non-continuous, dotted, dashed, repeating, periodic, random, constant width, varying width, overlapping, combinations thereof, and the like.

A linear pattern comprises one or more straight lines. For example, a linear pattern comprises a set of lines parallel to an edge of a substrate. A cross-hatched pattern is comprises a set of intersecting lines (e.g., parallel lines, curved lines). In some of these embodiments, the intersecting lines form an angle between about 0 degrees and about 180 degrees. In some of these embodiments, a first set of parallel lines intersect a second set of parallel lines. Within the first and second sets, the parallel lines are equally or unequally spaced apart. The set of lines have a uniform or varying frequency and/or density.

One or more patterned textures may be applied to a portion or entire surface of the substrate. For example, the ratio of a first surface area having a patterned texture to a second surface area having a non-patterned texture is between at least about 0.0001:1 and up to less than about 1:0 (corresponding to a surface completely covered by a patterned texture), between at least about 0.0001:1 and about 100:1, between at least about 0.001:1 and about 10:1, between at least about 0.01:1 and about 5:1, including all values and sub-ranges in-between. In some embodiments, the spatial distribution of one or more patterned textures across a plurality of regions of the substrate is symmetric (e.g., FIGS. 1A-1B, 2A-2C), asymmetric, periodic, non-periodic, random, combinations thereof, and the like. For example, the patterned texture comprises a random spatial distribution pattern within one or more regions of the substrate surface.

Figure 10A:
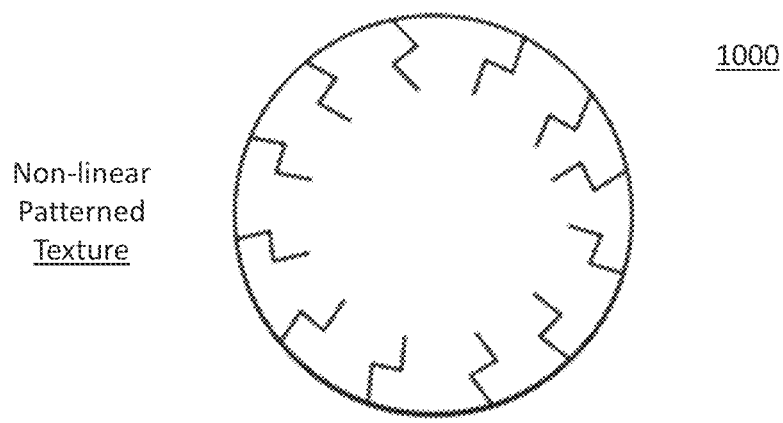
FIGS. 10A-10D and 10F-10I are illustrative schematic views of exemplary patterned textures.
Figure 10B:
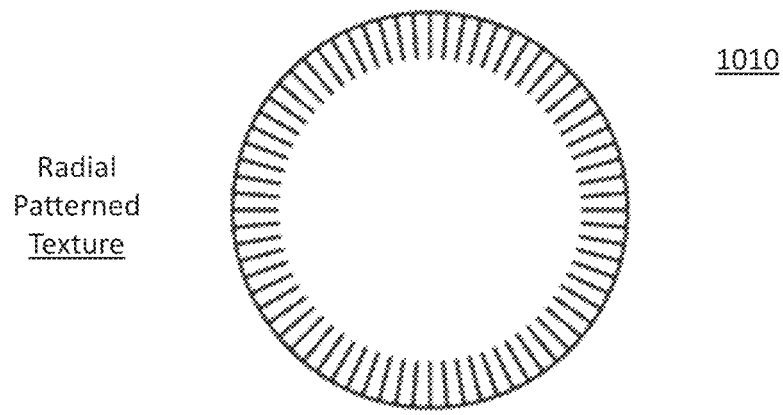
Figure 10C:
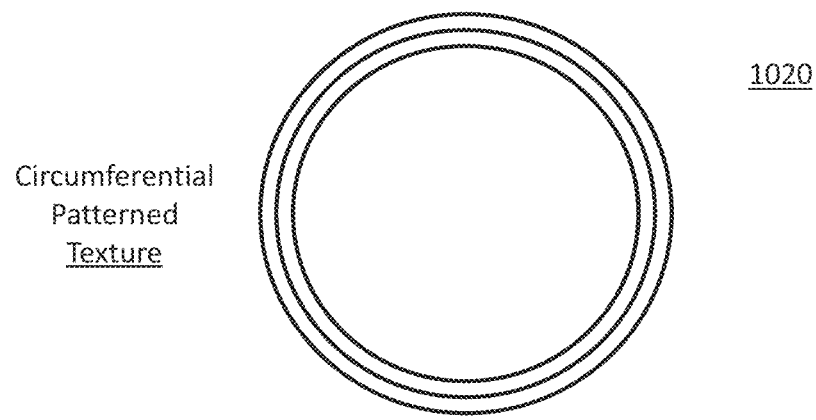
Figure 10D:
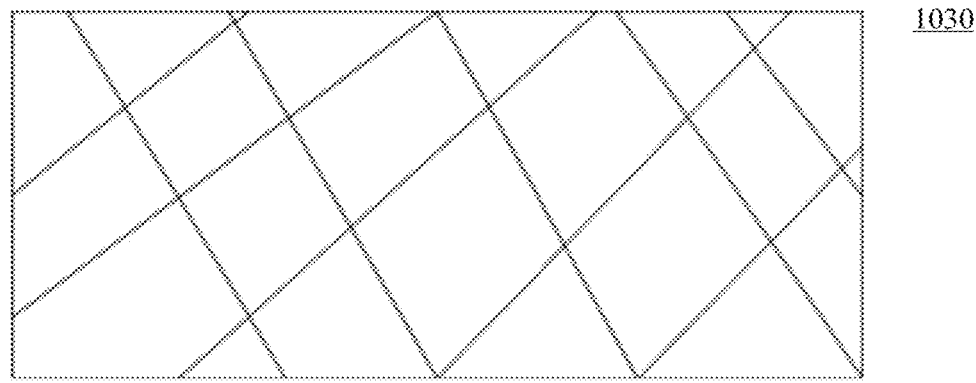
Figure 10E:
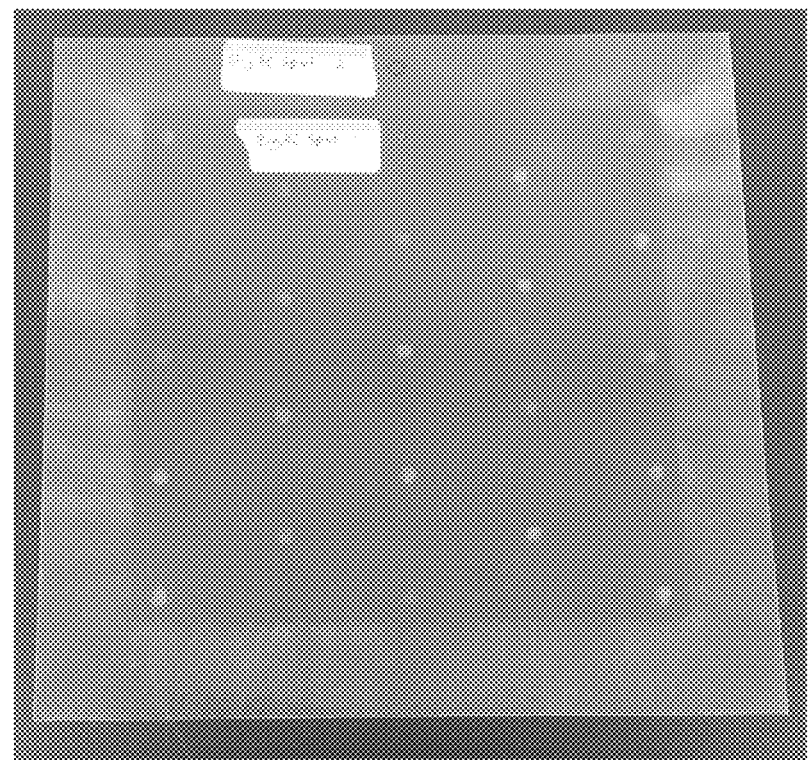
FIG. 10E is an illustrative view of another exemplary embodiment of a patterned texture on a substrate.
Figure 10F:
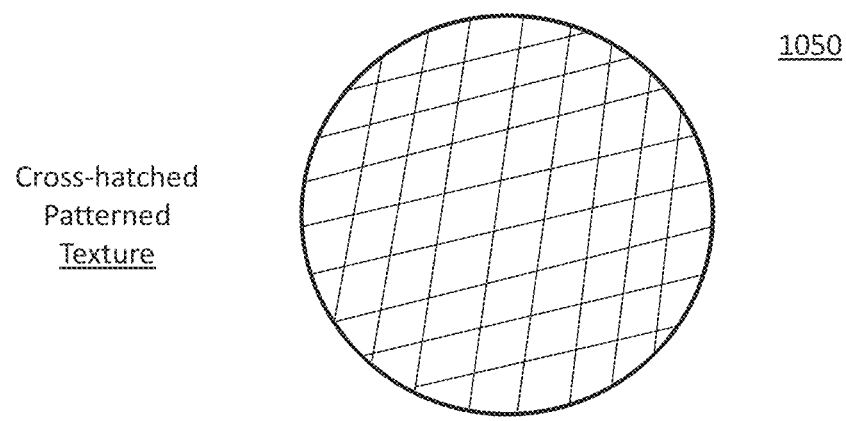
Figure 10G:
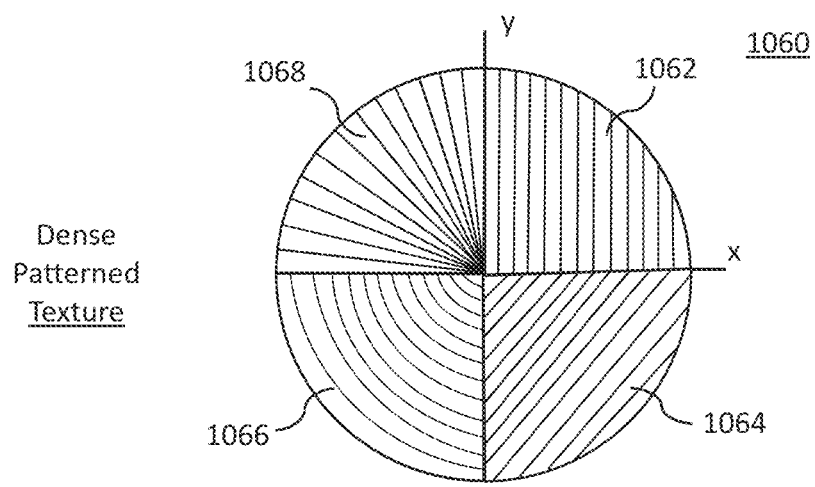
Figure 10H:
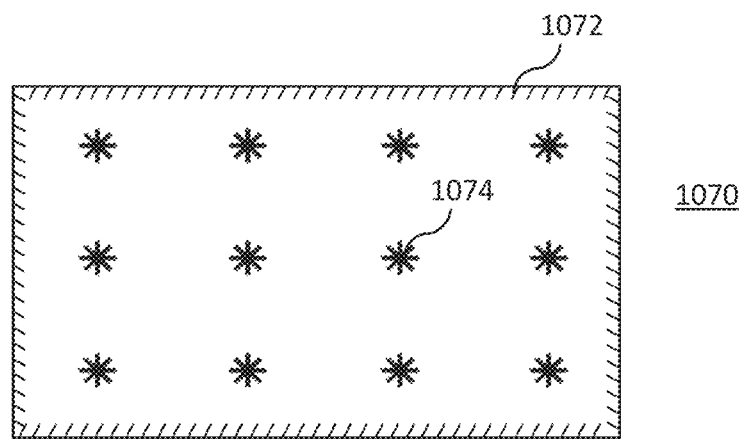

For example, FIG. 10H illustrates a patterned texture (1070) comprising a patterned texture regions and non-patterned texture regions. For example, a perimeter of a substrate may comprise a first patterned texture (1072) while an interior region may comprise a set of spaced apart second patterned textures (1074). This configuration may be configured to retain tissue across an entire substrate without providing a patterned texture entirely across the substrate. In other embodiments, one or more patterned textures may be applied across the substrate. FIGS. 18C and 18D depict a substrate comprising a patterned texture region and non-patterned texture region.

In some embodiments, one or more patterned textures of a substrate may depend on a shape of the substrate. For example, a channel or recess of a patterned texture may be substantially parallel to a surface of the substrate. That is, a circular substrate may comprise a patterned texture comprising a set of circular channels (e.g., FIGS. 2A-2C, 10C). Similarly, a rectangular substrate may comprise a set of linear channels extending in parallel to a lengthwise edge of the rectangular substrate (e.g., FIGS. 12-14).

In some embodiments, a region of a surface of the cell culture substrate has one or more curved and flat portions. In some embodiments, the surface of the substrate forms a convex shape. In some embodiments, a surface of the substrate forms a set of steps. The patterned texture may have soft or hard transitions between regions of differing heights. In some embodiments, one or more portions of the surface are angled relative to ground (on which the substrate is placed). Similarly, the cell culture substrate may have one or more curved and flat portions. For example, in such an embodiment, the edges of a cell culture substrate are raised (e.g., form a wall) such that the surface forms a concave (e.g., bowl-like) shape.

In some embodiments, a patterned texture substrate may be configured to promote a set of local cellular microenvironments across a surface of the substrate having different tissue proliferation, commitment differentiation, maturation, and viability characteristics based on patterned texture characteristics, as described herein, such as topology, size, orientation, periodicity, and the like. One or more patterned textures of a substrate may be based on a cell type to be grown over the patterned texture. For example, a patterned texture substrate comprising a set of periodic round recesses comprising a diameter of between about 10 nm and about 100 nm may be configured to promote myotube formation from myoblasts.

In some embodiments, a plurality of cell types may be disposed over a substrate comprising a plurality of corresponding patterned textures. For example, a respective patterned texture may be configured for each of myoblast tissue, connective tissue, and adipose tissue to promote growth, adhesion, and retention of a comestible meat product.

In some embodiments, the physical dimensions of the patterned texture depends on the dimensions of the substrate. For example, the depth of a set of channels on the surface may increase monotonically away from a center of the substrate. That is, a depth of the patterned texture increases closer to the edge of the substrate. This allows for one or more of retention and release of cells (e.g., cell sheet) from the substrate. For example, a deeper channel near an edge of the substrate provides stronger mechanical interaction (e.g., adhesion) of the surface to the cells compared to adhesion at a central region of the substrate having a non-patterned texture surface.

In some embodiments, one or more patterned textures may be configured to generate a predetermined fluid flow pattern (e.g., convection pattern, flow path) over the substrate under predetermined conditions (e.g., within a predetermined range of fluid flow rates). For example, a substrate comprising a fish scale like patterned texture may generate smooth (e.g., laminar) fluid flow in a first direction but generate turbulent flow in a second direction opposite to the first direction. In some embodiments, the patterned texture may increase a surface area of a substrate that may increase the attachment and/or retention of particles (e.g., growth media nutrients) and cells to the substrate. For example, the patterned texture may further generate micro-turbulences in fluid (e.g., growth media) flow that may increase the efficiency of metabolic exchanges.

In some embodiments, fluid flow (e.g., growth media, cell culture media) over cells aligned with a direction of the patterned texture may aid detachment and release of the cells from the substrate. Moreover, the presence of non-patterned texture regions allows for visual observations of the cells and tissues during culture. In some embodiments, a flow of the cell culture media delivered to the substrate is perpendicular to at least one patterned texture of the substrate. Flowing media perpendicular to the texture can reduce cell sheet detachment, compared to flowing parallel to the texture.

The cell culture substrates described herein support growth and retention of cells including, but not limited to, cells comprising one or more of endoderm, mesoderm, ectoderm, and combinations thereof. In some embodiments, cells comprise one or more cells from livestock (e.g. bovine, porcine, ovine, caprine), poultry (e.g. avian), game, aquatic animal species, and the like. In some embodiments, cells comprise one or more of myoblasts, mesangioblasts, myofibroblasts, mesenchymal stem cells, hepatocytes, fibroblasts, pericytes, adipocytes, epithelial, chondrocytes, osteoblasts, osteoclasts, pericytes, pluripotent stem cells, somatic stem cells, and endothelial cells. The cell types described herein further encompass any of their states of differentiation. For example, the cells include myoblasts, myotubes, mature skeletal muscle, fibroblasts, tissue that includes cells and secreted extracellular matrices, adipocytes, adipose tissue, epithelial cells, epithelial tissue, vascular endothelium, combinations thereof, and the like. In some embodiments, cells may comprise vertebrate cells or non-vertebrate cells. In some embodiments, cells may comprise non-mammalian cells (e.g., insect cells, avian cells, fish cells, reptile cells, invertebrate cells). In some embodiments, cells may be genetically altered from their native state (e.g., include a genomic substitution insertion, deletion or recombination).

In some embodiments, one or more patterned textures may be configured to facilitate sterilization of the substrate which may promote higher yields and efficient large scale production of a comestible meat product. For example, a patterned texture surface may comprise a set of parallel linear channels be configured to drain and/or retain a fluid (e.g., cleaning fluid, disinfection agent) for sterilization.

Exemplary Patterned Textures

FIGS. 1A-4C, 10A-10I, and 12A-17 are illustrative cell substrates having patterned textures on their respective surfaces. A population of cells grown on these exemplary substrates mechanically interact with the patterned textures formed on the substrates to increase adhesion and/or retention of cells to the substrate for a longer amount of time compared to a substrate not having a patterned texture surface while maintaining health and viability of the cells. In some embodiments, these cell substrates may be used to form a comestible meat product.

FIGS. 10A-10D depict illustrative schematic plan views of a set of patterned textures formed on a surface of a substrate. FIG. 10A illustrates a non-linear (e.g., zigzag) patterned texture (1000) comprising a set of channels each having a pair of bends (although any number of bends are contemplated). The portions of the channel between the bends may be linear or non-linear. In FIG. 10A, the channels are generally directed in a radial direction towards a center of the substrate. In some embodiments, the set of channels may be generally parallel to each other.

FIG. 10B illustrates a radial patterned texture (1010) comprising a set of channels extending in a radial direction defined by a set of lines extending from a common point (e.g., center of the substrate). The channels in FIG. 10B may have a uniform or non-uniform length, width, and density. In some embodiments, the radial patterned texture may extend to an edge of the substrate. A central region of the substrate may comprise a non-patterned surface. In some embodiments, the set of channels may be densely spaced. For example, each channel may be spaced apart from an adjacent channel between about 100 μm and about 1 mm. In some embodiments, a substrate comprising the radial patterned texture (1010) may have a diameter of up to about 3 cm. The radial patterned texture (1010) may allow preparation of a cell sheet across the entire radial patterned texture (1010).

FIG. 10C illustrates a circumferential patterned texture (1020) comprising a set of substantially parallel channels formed in a circumferential (e.g., circular) direction. Each channel need not form a continuous circle, and may form one or more arcs. In some embodiments, the circumferential patterned texture may comprise one or more spiral segments. The channels in FIG. 10C may have a uniform or non-uniform radius of curvature, length, width, and density. In some embodiments, the circumferential patterned texture may extend to an edge of the substrate. A central region of the substrate may comprise a non-patterned surface. In some embodiments, the set of channels may be densely spaced. For example, each channel may be spaced apart from an adjacent channel between about 100 μm and about 1 mm. In some embodiments, a substrate comprising the circumferential patterned texture (1020) may have a diameter of up to about 3 cm. The circumferential patterned texture (1020) may allow preparation of a cell sheet across the entire circumferential patterned texture (1020).

Each of the patterned textures in FIGS. 10A-10C are formed along a perimeter of its corresponding substrate (e.g., formed along a circumference of the substrate) with a central circular portion of the substrate comprising a non-patterned texture surface. Generally, one or more of the channels may intersect or may be non-intersecting. One or more of a depth and width of each channel may vary along a length of the channel. The length, depth, width, and frequency of the channels may be substantially uniform or may vary.

FIGS. 10D and 10F illustrate cross-hatched patterned textures (1030, 1050) comprising a set of intersecting channels. For example, a first set of substantially parallel channels extend across the substrate and intersect one or more channels of a second set of substantially parallel channels. The first and second set of channels may cross each other to form any predetermined angle at each intersection. For example, the first and second set of channels may intersect to form an angle between greater than 0° and less than 180°, between greater than 0° and about 150°, between about 30° and about 150°, between about 60° and about 120°, and between about 30° and about 90°, including all values and sub-ranges in-between.

One or more of a depth and width of each channel may vary along a length of the channel. The length, depth, width, and frequency of the channels may be substantially uniform or may vary. In some embodiments, the cross-hatched patterned texture (1030) may be applied up to and including an entire surface of a substrate. In some embodiments, a spacing between adjacent parallel channels may be between about 30 mm and about 7 mm, which may improve retention of cells (e.g., cell sheet) on the substrate.

FIG. 10E illustrates a linear and spot patterned texture (1040). A perimeter of a square substrate includes a set of linear channels having a generally horizontal or vertical direction except towards the corners where the channels are angled towards a center of the substrate. Between the linear channels, a set of spaced-apart spots (e.g., circular dots) are formed in an array. The linear and spot patterned texture (1040) is formed in FIG. 10E using an 800 grit abrasive material.

FIGS. 10A-10C depict substrates having a circular disk shape and FIGS. 10D-10E have a substrate with a rectangular shape, but the patterned textures illustrated and described herein are not limited to these pattern-substrate pairings. For example, radial and circumferential patterned textures may be formed on a rectangular substrate or a substrate having any shape. In some embodiments, one or more patterned textures may be laid over each other or formed on different regions of the substrate.

Figure 10I:
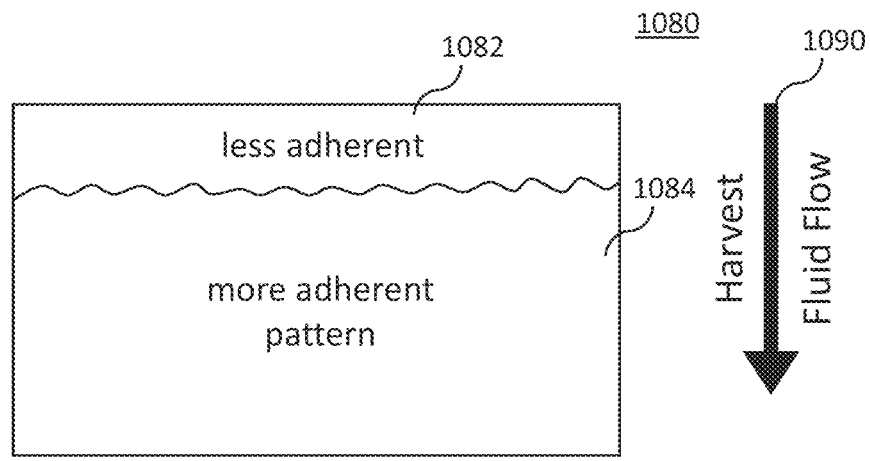

FIGS. 10G-10I depict illustrative schematic plan views of a set of patterned textures formed on a surface of a substrate. FIG. 10G illustrates a plurality of patterned textures (1060) comprising a set of channels. For the sake of example, a different patterned texture is provided for each quadrant of a substrate having any predetermined shape (e.g., square, rectangle, curved). For example, a first set of channels (1062) may comprise linear and parallel channels extending along a first direction (e.g., along the y-axis) and a second set of channels (1064) may comprise linear and parallel channels extending along a second direction different from the first direction. A third set of channels (1066) may comprise substantially parallel channels formed in a circumferential (e.g., circular) direction such as described with respect to FIG. 10C. A fourth set of channels (1068) may comprise linear channels extending radially from a central point (e.g., center of a substrate). In some embodiments, the patterned textures (1060) may extend to an edge of the substrate. One or more regions of the substrate may comprise a non-patterned surface. In some embodiments, the set of channels may be densely spaced. For example, each channel may be spaced apart from an adjacent channel between about 1 μm and about 1 mm. The patterned texture (1060) may allow preparation of a cell sheet across the entire patterned texture (1060).

In some variations, a patterned texture may be configured to facilitate separation of a cell sheet from a substrate by including regions having different adhesion characteristics. FIG. 10I illustrates a patterned texture (1080) comprising a first patterned texture region and a second patterned texture region. For example, a first region (1082) of a substrate may comprise a first patterned texture while a second region (1084) may comprise a second patterned texture. The first patterned texture may have a first tissue adhesion quality and the second patterned texture may have a second tissue adhesion quality greater than the first tissue adhesion quality. That is, cells may more strongly bond to the second patterned texture region than the first patterned texture region. The patterned texture (1080) may be configured to facilitate cell sheet separation from the substrate.

In some embodiments, the patterned texture (1080) may be configured to promote separation of an intact cell sheet from the substrate. For example, once a cell sheet has reached predetermined criteria (e.g., grown to a predetermined size, shape, volume, density), fluid configured to separate the tissue from the substrate may flow in a predetermined direction (1090) over the tissue (e.g., cell sheet) grown on the patterned texture (1080). Separation of the cell sheet may begin with fluid that initially contacts the tissue adhered to the first region (1082) of the substrate since it has a lesser adhesion quality than the second region (1084). As the first region tissue separates from the substrate, the tissue adhered to the second region (1084) of the substrate may separate from the substrate due to the fluid flow and the pulling forces generated by the first region tissue.

Figure 1B:
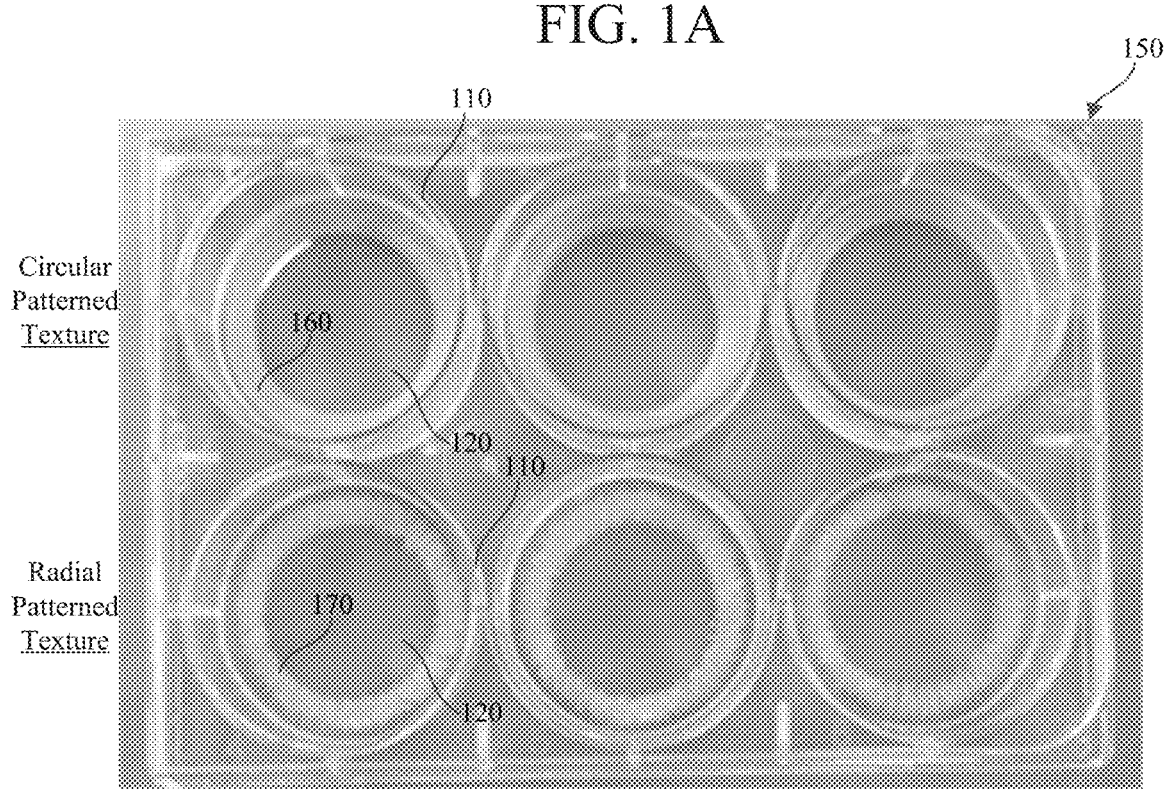

FIGS. 1A and 1B each depict plan views of a set of cell culture substrates (120) placed on a polystyrene plate (100, 150) having a set of six wells (110). The substrates (120) comprise a substantially planar circular disk shape configured for insertion into a corresponding well (110). In FIG. 1A, a top row of substrates (120) has a first patterned texture (130) formed on its respective surface, and a bottom row of substrates (120) has a second patterned texture (140) formed on its respective surface. Likewise, in FIG. 1B, a top row of substrates (120) has a third patterned texture (160) formed on its respective surface, and a bottom row of substrates (120) has a fourth patterned texture (170) formed on its respective surface. Each of the patterned textures (130, 140, 160, 170) shown in FIGS. 1A-1B are toroidal and are formed along a perimeter of the circular substrate (120) while a circular portion of the substrate (120) comprises a non-patterned texture surface. FIG. 1A illustrates patterned textures (130, 140) comprising a circumferential (e.g., circular) direction. FIG. 1B illustrates patterned textures (160, 170) comprising a radial direction defined by a set of lines extending from a common point (e.g., center of the substrate (120)).

In this manner, a population of cells (not shown) grown in the wells (110) mechanically interacts with the patterned textures (130, 140, 160, 170) formed on a perimeter surface of the circular substrate (120) to increase adhesion of cells to the substrate (120) for a longer amount of time compared to a substrate not having a patterned texture surface. In some embodiments, the patterned texture formed along the perimeter surface of the substrate (120) aids detachment of the cells from the substrate (120). For example, a mechanical shear device (e.g., cell scraper) may be used to detach cells along the radial lines formed by the patterned textures (140, 170).

The first patterned texture (130) and second patterned texture (140) in FIG. 1A are formed on a surface of the substrate (120) by applying 800 grit abrasive material (e.g., sandpaper, aluminum oxide paper, silicon carbide film) to the surface of the substrate (120). The first patterned texture (130) is formed in a circumferential direction along, for example, a perimeter of the substrate (120). Similarly, the third patterned texture (160) and fourth patterned texture (170) in FIG. 1B are formed on a surface of the substrate (120) by applying a 60 grit abrasive material to the surface of the substrate (120).

Although each of the substrates (120) depicted in FIGS. 1A-1B includes one patterned texture, the substrates described herein may include a plurality of regions corresponding to a plurality of patterned textures. For example, a first region (e.g., circular inner portion) may be formed using a first processing technique (e.g., mechanical abrasion) and a second region (e.g., toroidal outer portion) may be formed using a second processing technique different from the first processing technique (e.g., chemical etching and printing) such that the first and second regions have different surface texture characteristics. In some embodiments, the toroidal shape of the patterned texture is formed on a non-circular substrate such as a square substrate, rectangular substrate, curved substrate, etc. The arrangement and configuration of a plurality of patterned textures is described in more detail herein with respect to cell sheet size. In some embodiments, a plurality of processing techniques may be applied within a same region.

Figure 2A:
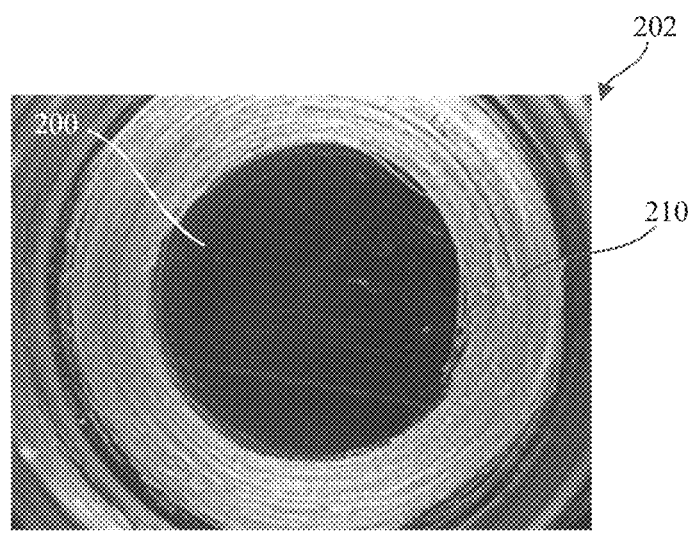
FIGS. 2A-2C are illustrative views of exemplary embodiments of cell culture substrates disposed in corresponding wells.
Figure 2B:
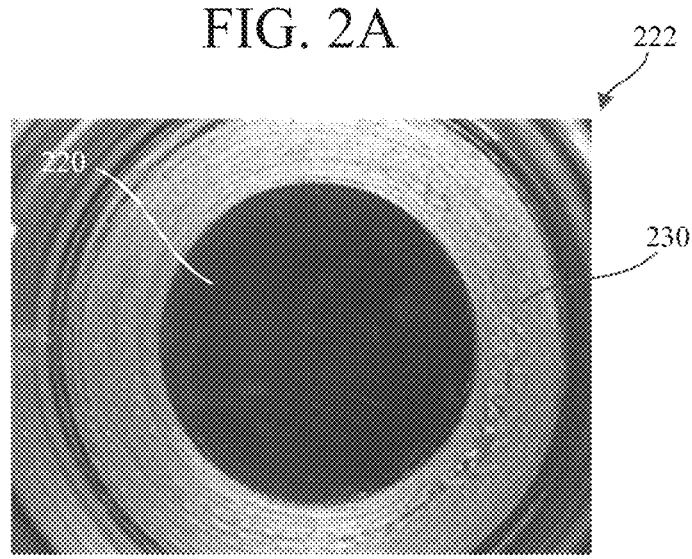
Figure 2C:
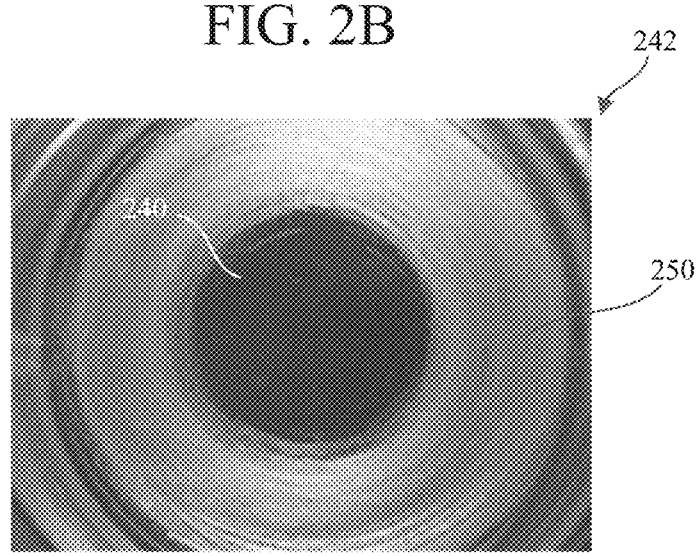

FIGS. 2A, 2B, and 2C each depict plan views of cell culture substrates (200, 220, 240) placed in corresponding wells (202, 222, 242). The substrates (200, 220, 240) comprise a substantially planar circular disk shape. A first cell culture substrate (200) has a first patterned texture (210) formed on its surface, a second cell culture substrate (220) has a second patterned texture (230) formed on its surface, and a third cell culture substrate (240) has a third patterned texture (250) formed on its surface. Each of the patterned textures (210, 230, 250,) shown in FIGS. 2A-2C are toroidal and are formed along a perimeter of a respective circular substrate (200, 220, 240) while an inner circular portion of the substrate (200, 220, 240) comprises a non-patterned texture surface. In this manner, a population of cells (not shown) grown in the wells (202, 222, 242) mechanically interacts with the patterned textures (210, 230, 250) formed on a perimeter surface of the circular substrate (200, 220, 240) to increase adhesion of cells to the substrate (200, 220, 240) for a longer amount of time compared to a substrate not having a patterned texture surface.

The first patterned texture (210) and third patterned texture (250) in FIGS. 2A and 2C is formed on a surface of the substrate (200) by applying respective 60 grit and 800 grit abrasive material (e.g., sandpaper, aluminum oxide paper, silicon carbide film) to the surface of the substrate (200). The second patterned texture (230) in FIG. 2B is formed on a surface of the substrate (220) by applying 150 grit abrasive material to the surface of the substrate (220). The patterned textures (210, 230, 250) are each formed in a circumferential direction along, for example, a perimeter of a respective substrate (200, 220, 240).

Figure 3A:
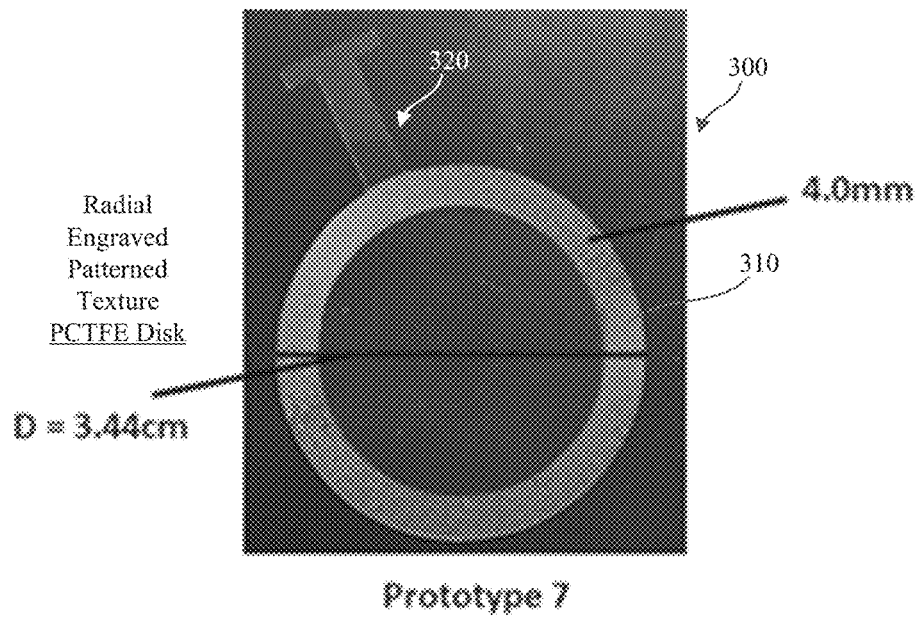
FIG. 3A is an illustrative view of an exemplary embodiment of a cell culture substrate, comprising a radial patterned texture.

FIG. 3A is plan view of a circular cell culture substrate (300) composed of polychlorotrifluoroethylene (PCTFE). The substrate (300) comprises a diameter of about 3.44 cm and has a toroidal patterned texture (310) comprising a width of about 4.0 mm. The patterned texture (310) has a radial direction and is formed, for example, by one or more of engraving and die cutting using a die cutting apparatus. In some embodiments, the cell culture substrate (300) is coupled to a projection (320) (e.g., tab, handle) configured to facilitate one or more of insertion and removal of the substrate (300) from a well (340). For example, a user may manipulate the substrate (300) within a well (340) by a holding a portion of the projection (320). In some embodiments, the cell culture substrate (300) does not include the projection (320) to reduce interference with test equipment.

Figure 3B:
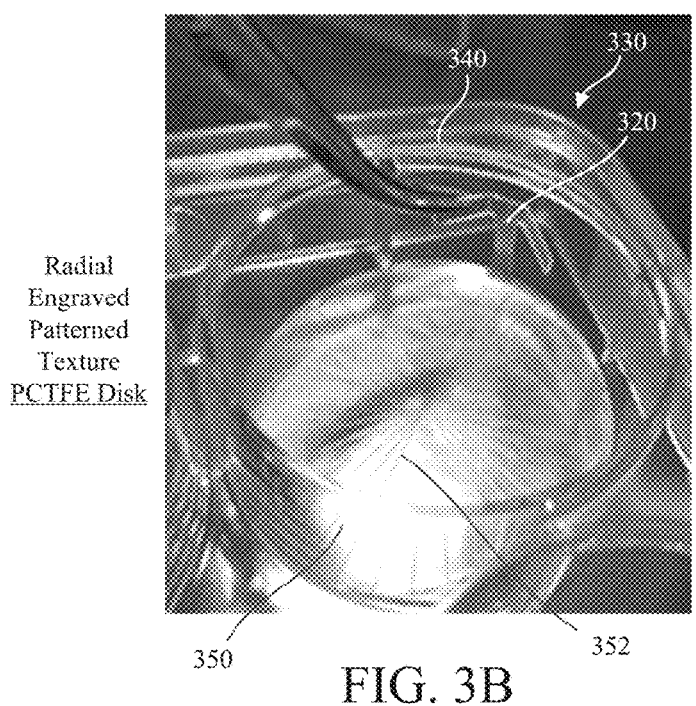
FIG. 3B is an illustrative view of another exemplary embodiment of a cell culture substrate with a radial patterned texture placed in a well.
Figure 3C:
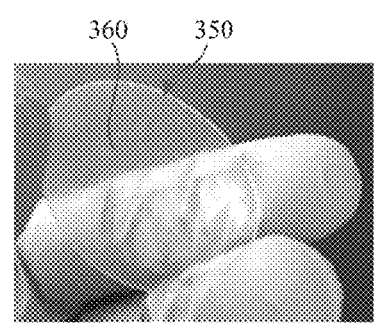
FIG. 3C is an illustrative view of an exemplary embodiment of a cell sheet grown on a cell culture substrate.

FIG. 3B is a perspective view of a cell culture substrate (350), as described in FIG. 3A above, placed in a well (340) of a multi-well plate (330). In FIG. 3B, a patterned texture (352) is placed over an entire surface of the substrate (350) and has a radial direction. FIG. 3C is a perspective view of a 12 day-old cell sheet (360) (cell sheet of fibroblast cells) grown and attached to the cell culture substrate (350) having the patterned texture (352) and which covered the entire surface of the substrate (350). In related embodiments, adherent cell sheets of greater than 30 days are formed using fibroblasts, myogenic cells, and combinations of fibroblasts and myogenic cells.

Figure 4A:
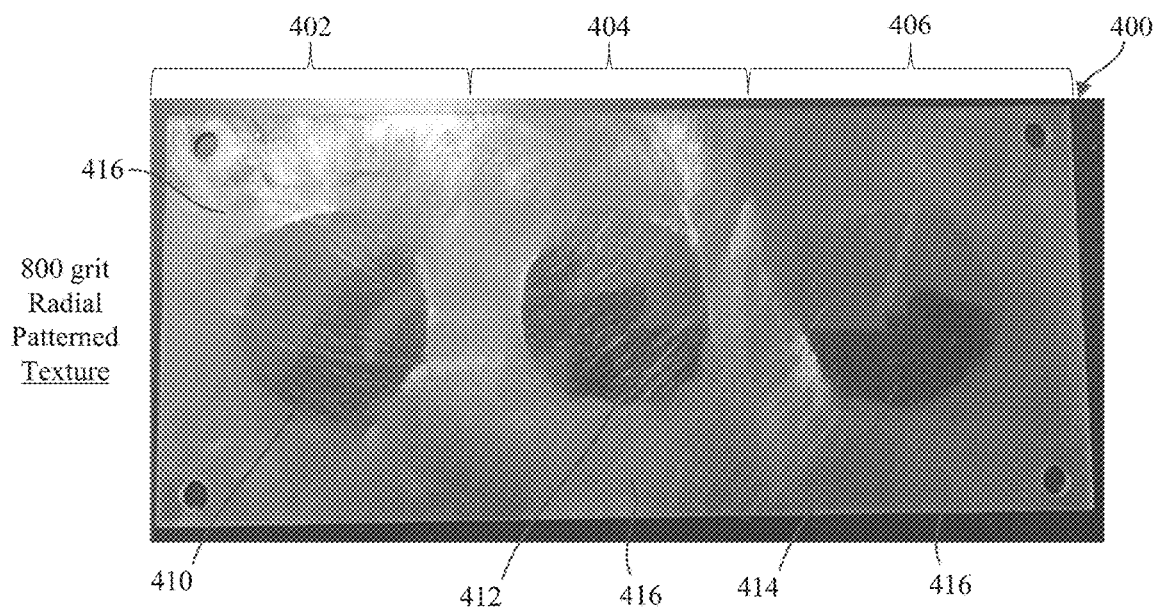
FIGS. 4A-4C are illustrative views of exemplary cell culture substrates comprising a plurality of regions of patterned textures.

FIG. 4A depicts a plan view of a rectangular cell culture substrate (400) composed of polyetherimide (PEI). The substrate (400) comprises a plurality of regions (402, 404, 406) corresponding to a plurality of patterned textures (416). The patterned textures (416) has a radial direction extending from a respective center of each region (402, 404, 406). A circular portion (410, 412, 414) of each region (402, 404, 406) includes the radial patterned texture (416). The first patterned texture (416) in FIG. 4A is formed on a surface of the substrate (400) by applying 800 grit abrasive material (e.g., sandpaper, aluminum oxide paper, silicon carbide film) to the surface of the substrate (200) in a radial direction.

Figure 4B:
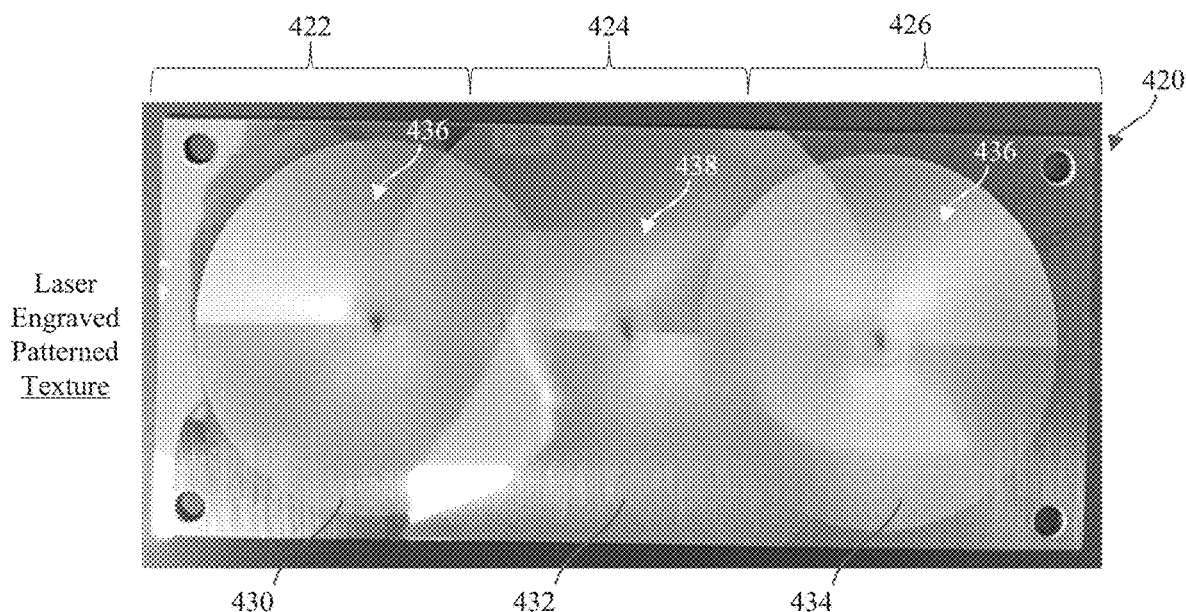

FIG. 4B depicts a plan view of a rectangular cell culture substrate (420) composed of stainless steel (e.g., 304 or 316 stainless steel). The substrate (420) comprises a plurality of regions (422, 424, 426) corresponding to a plurality of patterned textures (436, 438). The patterned textures (436, 438) have a radial direction extending from a respective center of each region (430, 432, 434). A central circular portion of each region (430, 432, 434) includes the radial patterned texture (416) while other portions of the substrate are non-patterned. In some embodiments, the patterned textures (436, 438) in FIG. 4B are engraved on a surface of the substrate (420) by using a solid-state laser (e.g., Nd:YAG laser) or any suitable laser (e.g., semiconductor diode laser, fiber laser). In FIG. 4B, the patterned textures (436, 438) partially overlaps each other over the surface of the substrate (420). For example, portions of a second patterned texture (438) overlap portions of a first patterned texture (436) in a manner similar to a Venn diagram. The patterned textures in FIGS. 4A-4B have a diameter of between about 30 mm and about 40 mm.

A population of cells (not shown) grown on the substrate (400, 420) mechanically interacts with the patterned textures (416, 436, 438) formed on the substrate (400, 420) to increase adhesion of cells to the substrate (400, 420) for a longer amount of time compared to a substrate not having a patterned texture surface while maintaining health and viability of the cells. In some embodiments, the cell culture substrates (400, 420) are used in scalable parallel-plate bioreactors.

Figure 4C:
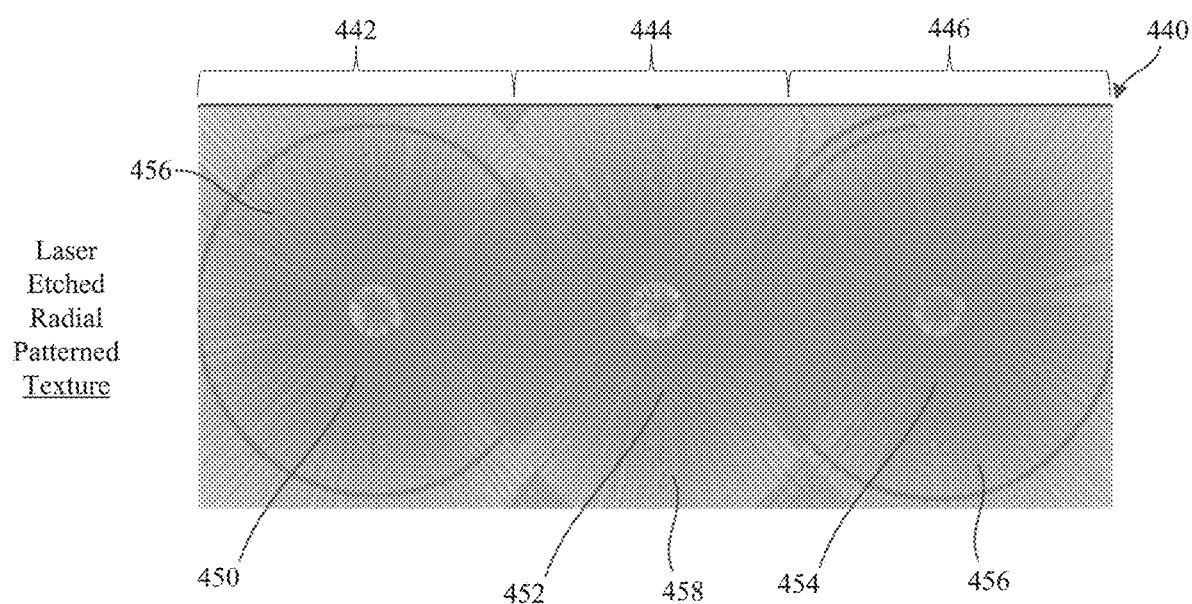

FIG. 4C depicts a schematic plan view of a rectangular cell culture substrate (440). The substrate (440) comprises a plurality of regions (442, 444, 446) corresponding to a plurality of patterned textures (456, 458). The patterned textures (456, 458) have a radial direction extending from a respective center of each region (450, 452, 454). A central circular portion of each region (450, 452, 454) includes the radial patterned texture (456, 458). In some embodiments, the patterned textures (456, 458) in FIG. 4C are engraved on a surface of the substrate (440) by using a solid-state laser (e.g., Nd:YAG laser) or any suitable laser (e.g., semiconductor diode laser, fiber laser). In FIG. 4C, the patterned textures (456, 458) partially overlaps each other over the surface of the substrate (440). For example, portions of a second patterned texture (458) overlap portions of a first patterned texture (456) in a manner similar to a Venn diagram. The first patterned texture (456) includes a radial patterned texture and a circumferential patterned texture that overlap each other.

Figure 12A:
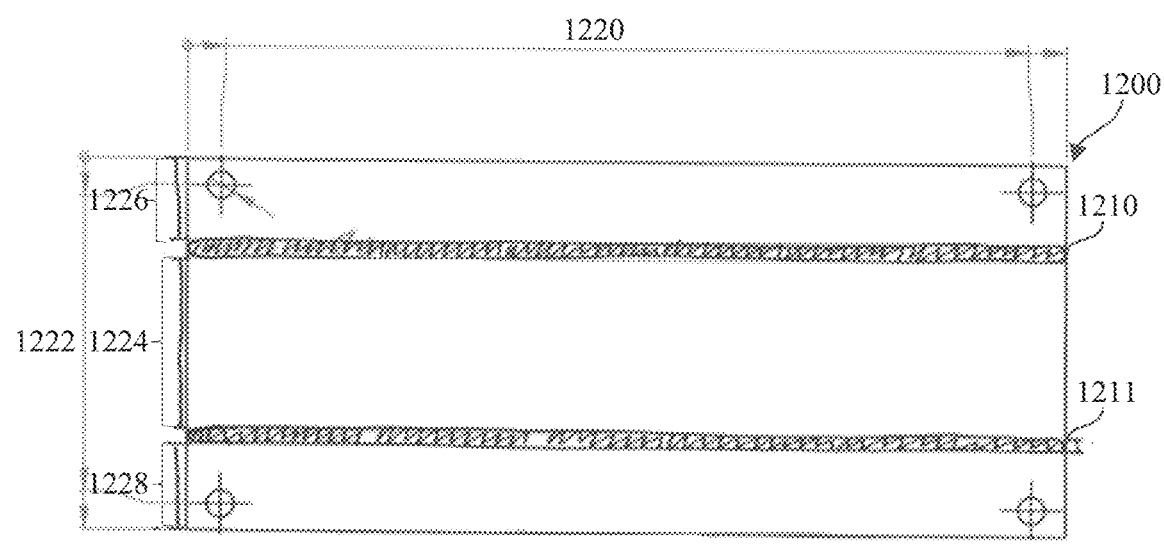
FIG. 12A is an illustrative view of an exemplary patterned texture on a substrate.

FIG. 12A depicts a schematic plan view of a rectangular cell culture substrate (1200) composed of #8 mirror polished stainless steel (e.g., 304 or 316 stainless steel). The substrate (1200), for example, has a length (1220) of about 13 cm, a width (1222) of about 5.5 cm, and a thickness of about 1.5875 mm. The substrate (1200) comprises a set of patterned textures (1210, 1211). The patterned textures (1210, 1211) have a linear direction extending across an entire length of the substrate (1200). In FIG. 12A, a first patterned texture (1210) is spaced apart from a second patterned texture (1211) by a first distance (1224). The first patterned texture (1210) is spaced apart from an edge of the substrate (1200) by a second distance (1226) and the second patterned texture (1211) is spaced apart from an edge of the substrate (1200) by a third distance (1228). For example, the first distance (1224) is about 26 mm, and the second and third distances (1226, 1228) are each about 12.5 mm. The patterned textures (1210, 1211) each comprise a channel (e.g., groove, recesses, etc.) having a width of about 2 mm and a depth of about 0.2 mm. For example, the substrate (1200) is machine grooved to form the patterned textures (1210, 1211).

Figure 12B:
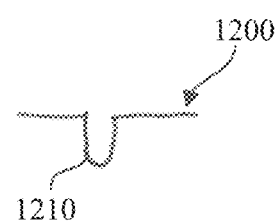
FIG. 12B is a cross-sectional side view of an exemplary patterned texture.

FIG. 12B is a cross-sectional side view of a patterned texture (1210) formed on a surface of a substrate (1200). In particular, a cross-section of the channel is shown having a width of about 2 mm and a depth of about 0.2 mm. The channel in FIG. 12B has a rounded bottom portion and a sharp edge (e.g., shoulder) where the channel meets the surface. For example, an uppermost portion of the channel (e.g., channel edge) may form an angle of about 90° with respect to the surface. Each of the channels illustrated in FIGS. 13-17 have a similar configuration as the channel in FIG. 12B.

Figure 13:
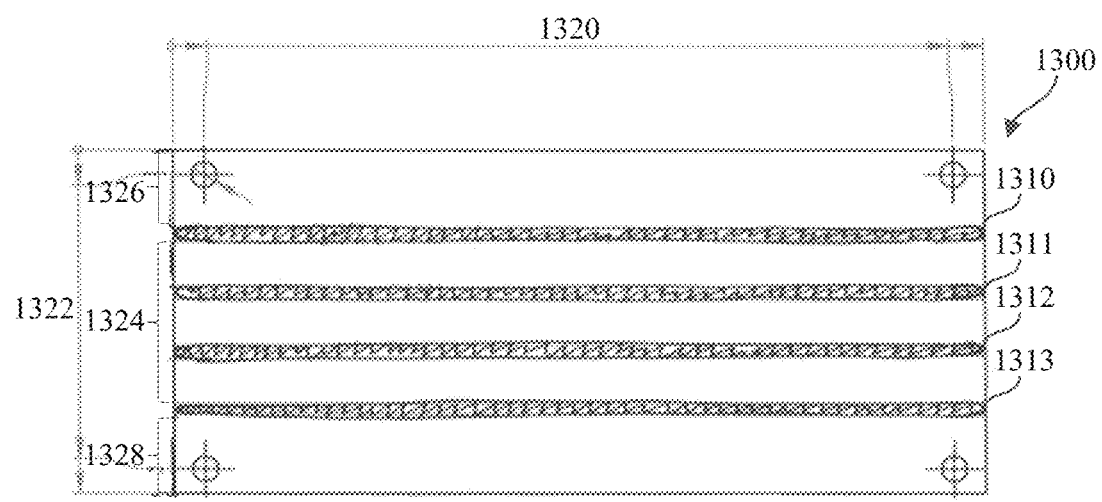
FIG. 13 is an illustrative view of an exemplary patterned texture on a substrate.

FIG. 13 depicts a schematic plan view of a rectangular cell culture substrate (1300) composed of #8 mirror polished stainless steel (e.g., 304 or 316 stainless steel). The substrate (1300), for example, has a length (1320) of about 13 cm, a width (1322) of about 5.5 cm, and a thickness of about 1.5875 mm. The substrate (1300) comprises a set of patterned textures (1310, 1311, 1312, 1313). The patterned textures (1310, 1311, 1312, 1313) have a linear direction extending across an entire length of the substrate (1300). In FIG. 13, the patterned textures (1310, 1311, 1312, 1313) extend widthwise along the substrate (1300) by a first distance (1324). The first patterned texture (1310) is spaced apart from an edge of the substrate (1300) by a second distance (1326) and the fourth patterned texture (1313) is spaced apart from an edge of the substrate (1300) by a third distance (1328). For example, adjacent patterned textures are each separated by about 7.3 mm, and the second and third distances (1326, 1328) are each about 12.5 mm. The patterned textures (1310, 1311, 1312, 1313) each comprise a channel (e.g., groove, recesses, etc.) having a width of about 2 mm and a depth of about 0.2 mm, as shown in FIG. 12B. In some embodiments, the substrate (1300) is machine grooved to form the patterned textures (1310, 1311, 1312, 1313).

Figure 14:
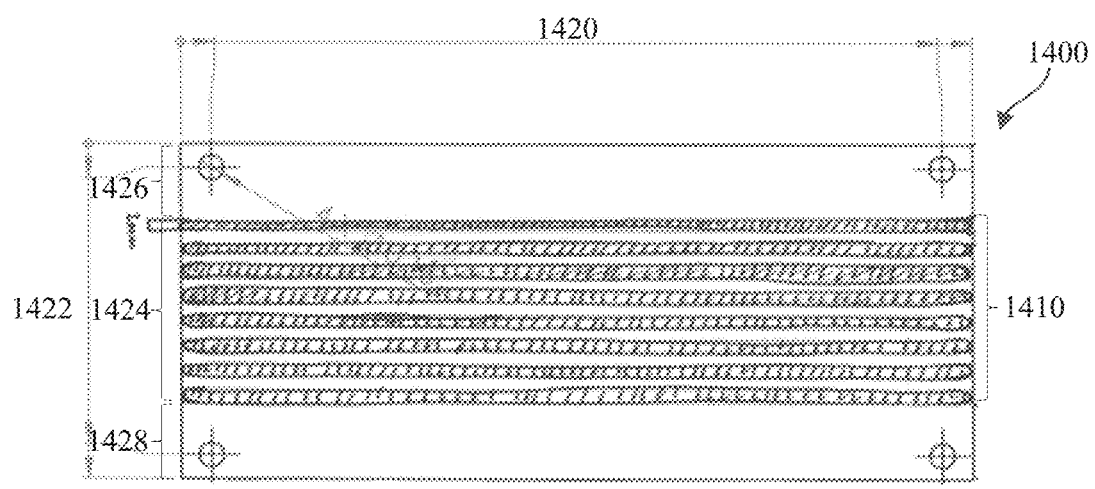
FIG. 14 is an illustrative view of an exemplary patterned texture on a substrate.

FIG. 14 depicts a schematic plan view of a rectangular cell culture substrate (1400) composed of #8 mirror polished stainless steel (e.g., 304 or 316 stainless steel). The substrate (1400), for example, has a length (1420) of about 13 cm, a width (1422) of about 5.5 cm, and a thickness of about 1.5875 mm. The substrate (1400) comprises a set of patterned textures (1410) including eight parallel and evenly-spaced channels. The patterned textures (1410) have a linear direction extending across an entire length of the substrate (1400). In FIG. 14, the patterned textures (1410) extend widthwise along the substrate (1400) by a first distance (1424). A first patterned texture nearest a first edge of substrate is spaced apart from the first edge by a second distance (1426) and an eighth patterned texture (1410) nearest a second edge is spaced apart from the second edge by a third distance (1428). For example, adjacent patterned textures are each spaced apart by about 2 mm, and the second and third distances (1426, 1428) are each spaced apart by about 12.5 mm. The patterned textures (1410) each comprise a channel (e.g., groove, recesses, etc.) having a width of about 2 mm and a depth of about 0.2 mm, as shown in FIG. 12B. In some embodiments, the substrate (1400) is machine grooved to form the set of patterned textures (1410).

Figure 15:
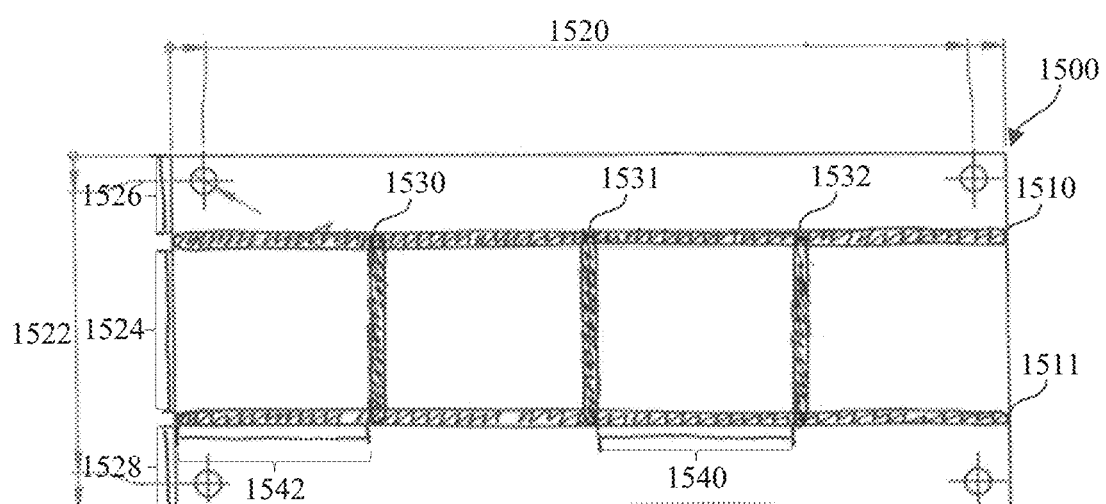
FIG. 15 is an illustrative view of an exemplary patterned texture on a substrate.

FIG. 15 depicts a schematic plan view of a rectangular cell culture substrate (1500) composed of #8 mirror polished stainless steel (e.g., 304 or 316 stainless steel). The substrate (1500), for example, has a length (1520) of about 13 cm, a width (1522) of about 5.5 cm, and a thickness of about 1.5875 mm. The substrate (1500) comprises a set of patterned textures (1510, 1511, 1530, 1531, 1532) including lengthwise and widthwise channels extending linearly and orthogonally to each other. The set of patterned textures (1510, 1511, 1530, 1531, 1532) include parallel first and second channels (1510, 1511) connected by parallel third, fourth, and fifth channels (1530, 1531, 1532). The first channel (1510) is spaced apart from the second channel (1511) by a first distance (1524). The first and second channels (1510, 1511) are spaced apart from respective edges of the substrate (1500) by respective second and third distances (1526, 1528). For example, the first distance is about 26 mm, and the second and third distances (1526, 1528) are each about 12.5 mm. The third, fourth, and fifth channels (1530, 1531, 1532) are spaced apart from each other by a fourth distance (1540) or spaced apart from an edge of the substrate by a fifth distance (1542). For example, the fourth and fifth distance is about 31 mm. The channels of the set of patterned textures (1510, 1511, 1530, 1531, 1532) each have a width of about 2 mm and a depth of about 0.2 mm, as shown in FIG. 12B. In some embodiments, the substrate (1500) is machine grooved to form the set of patterned textures (1510, 1511, 1530, 1531, 1532).

Figure 16:
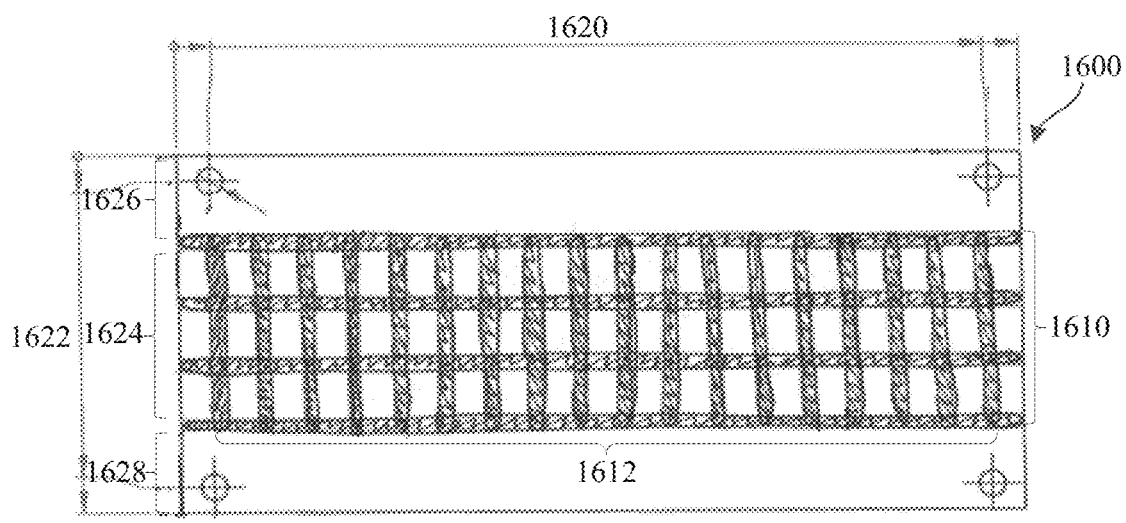
FIG. 16 is an illustrative view of an exemplary patterned texture on a substrate.

FIG. 16 depicts a schematic plan view of a rectangular cell culture substrate (1600) composed of #8 mirror polished stainless steel (e.g., 304 or 316 stainless steel). The substrate (1600), for example, has a length (1620) of about 13 cm, a width (1622) of about 5.5 cm, and a thickness of about 1.5875 mm. The substrate (1600) comprises a set of patterned textures (1610, 1612) including lengthwise and widthwise channels extending linearly and orthogonally to each other. The set of patterned textures (1610, 1612) include parallel lengthwise channels (1610) connected by parallel widthwise channels (1612). Adjacent lengthwise channels are spaced apart from each other by a first distance. Lengthwise edges of the substrate (1600) are spaced apart from their nearest channels by respective second and third distances. Adjacent widthwise channels are spaced apart from each other by a fourth distance. Widthwise edges of the substrate (1600) are spaced apart from their nearest widthwise channel by a fifth distance. For example, the first distance is about 7.3 mm, the second and third distances are each about 12.5 mm, the fourth distance is about 5 mm, and the fifth distance is about 4.5 mm. The lengthwise and widthwise channels of the set of patterned textures (1610, 1612) each have a width of about 2 mm and a depth of about 0.2 mm, as shown in FIG. 12B. In some embodiments, the substrate (1600) is machine grooved to form the set of patterned textures (1610, 1612).

Figure 17:
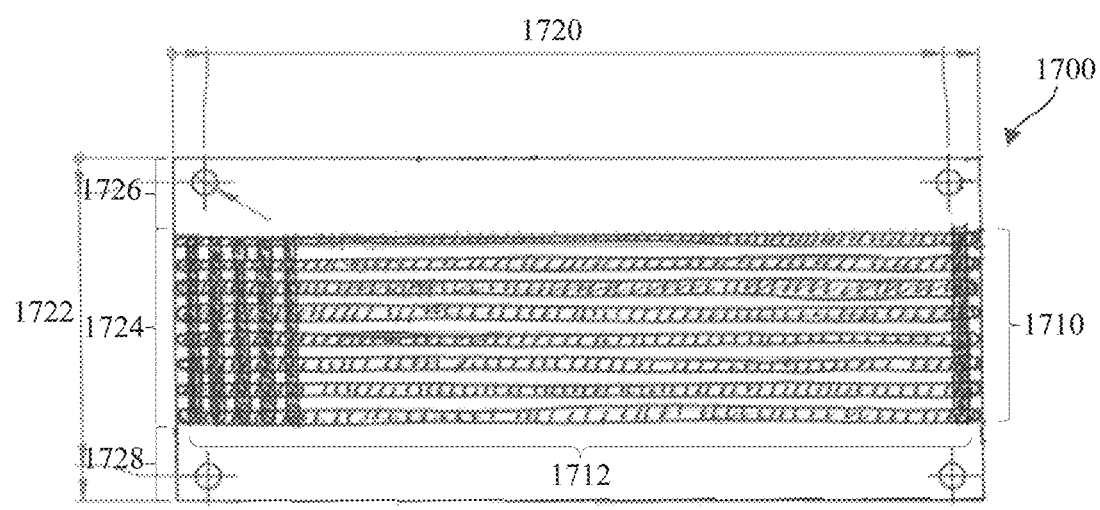
FIG. 17 is an illustrative view of an exemplary patterned texture on a substrate.

FIG. 17 depicts a schematic plan view of a rectangular cell culture substrate (1700) composed of #8 mirror polished stainless steel (e.g., 304 or 316 stainless steel). The substrate (1700), for example, has a length (1720) of about 13 cm, a width (1722) of about 5.5 cm, and a thickness of about 1.5875 mm. The substrate (1700) comprises a set of patterned textures (1710, 1712) including lengthwise and widthwise channels extending linearly and orthogonally to each other. The set of patterned textures (1710, 1712)

include parallel lengthwise channels (1710) connected by parallel widthwise channels (1712). For the sake of convenience, only a portion of the widthwise channels (1712) are illustrated in FIG. 17. The number and spacing of the widthwise channels (1712) extends lengthwise across the entire substrate (1700) in a similar manner to that shown in FIG. 16.

Adjacent lengthwise channels are spaced apart from each other by a first distance. Lengthwise edges of the substrate (1700) are spaced apart from their nearest channels by respective second and third distances. Adjacent widthwise channels are spaced apart from each other by a fourth distance. Widthwise edges of the substrate (1700) are spaced apart from their nearest widthwise channel by a fifth distance. For example, the first distance is about 2 mm, the second and third distances are each about 12.5 mm, the fourth distance is about 2 mm, and the fifth distance is about 2 mm. The lengthwise and widthwise channels of the set of patterned textures (1610, 1612) each have a width of about 2 mm and a depth of about 0.2 mm, as shown in FIG. 12B. In some embodiments, the substrate (1600) is machine grooved to form the set of patterned textures (1610, 1612).

Figure 5A:
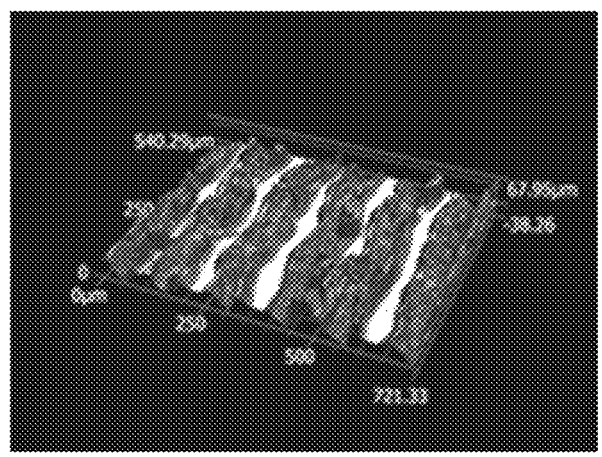
FIGS. 5A-5C are illustrative surface profilometry images of exemplary cell culture substrates comprising patterned textures.
Figure 5B:
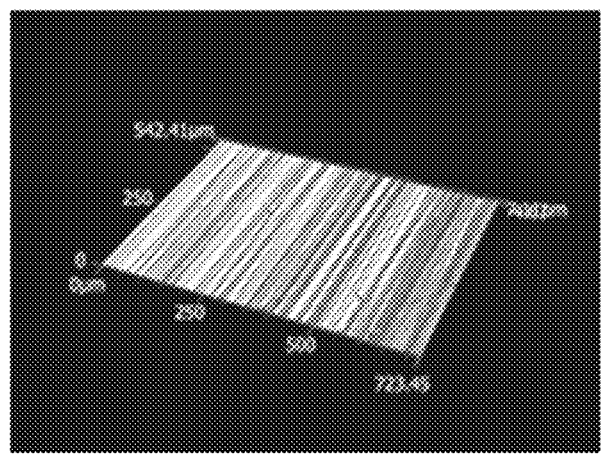
Figure 5C:
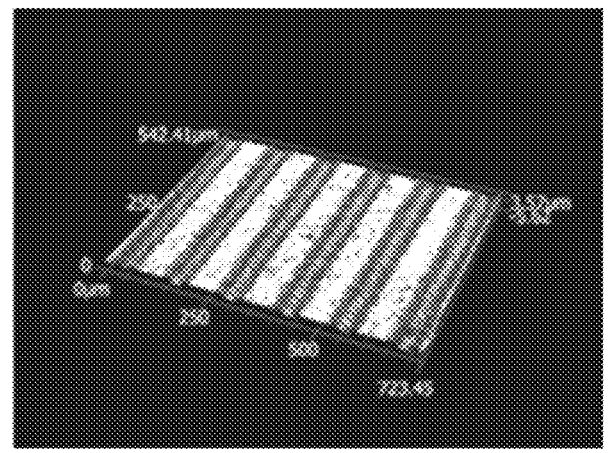

FIGS. 5A-5C are non-contact surface profilometry images of embodiments of a cell culture substrate that illustrate the physical characteristics of a patterned texture formed on a substrate. FIG. 5A illustrates a set of generally parallel channels on a surface of a PCTFE substrate formed by die cutting. In FIG. 5A, the channels have a width of between about 50 μm and about 150 μm and are separated by less than about 250 μm. FIG. 5B illustrates a set of generally parallel channels on a surface of a PCTFE substrate formed by using an 800 grit abrasive material. FIG. 5C illustrates a set of generally parallel channels on a surface of a stainless steel substrate formed by laser engraving. In FIG. 5C, the channels have a width of between about 40 μm and about 80 μm and are separated by between about 40 μm and about 80 μm. The uniformity of the patterned texture varies based on the manufacturing method employed.

Scalable Patterned Textures

Generally, the surface area of cells grown on the cell culture substrates described herein are scalable for a predetermined application such as production of comestible tissue or high throughput screening. A surface of a cell culture substrate is selected for one or more predetermined cell types to provide a set of predetermined cell growth, adhesion, retention, and release characteristics. However, the ability of a patterned texture to provide predetermined cell growth, adhesion, retention, and release characteristics depends on a size of the patterned texture and does not necessarily scale proportionally. For example, the dimensions of the radial patterned texture of FIG. 3A formed on a 3.44 cm diameter disk scaled to an 8 inch diameter disk with a corresponding 1 inch length radial channel does not maintain the same adhesion, retention, and release characteristics.

As described in more detail herein, one or more of the patterned textures may be formed in a unit of predetermined size (e.g., "unit cell"). A plurality of these unit cells may be arranged together and allow formation of a cell sheet of a desired size greater than that formed using conventional techniques and also maintain desired cell growth, adhesion, retention, and release characteristics. In some embodiments, a surface of a cell substrate comprises a plurality of regions (e.g., an array) where each region defines a repeatable unit having a patterned texture that is scaled (e.g., duplicated, repeated, extended, arranged) to generate cells having a predetermined surface area while maintaining one or more desired growth, adhesion, retention, and release characteristics. The repeatable units (e.g., unit cell) are arranged across a surface in any predetermined manner. For example, the plurality of regions are configured to aid release of a substantially whole cell sheet from the cell culture substrate at a predetermined time and/or cell state.

In some embodiments, each region includes one or more patterned textures and non-patterned portions. The plurality of regions of the cell substrate may form a mosaic or tile-like surface structure. For example, the patterned textures of one or more regions are repeated in a predetermined arrangement (e.g., a grid-like pattern) across a surface of a substrate or are arranged hierarchically. For example, the repeatable patterned texture of a region is scalable for multi-well plates having different sizes (e.g., 6 wells, 12 wells, 24 wells, 28 wells, 96 or more wells). As another example, the patterned texture of a set of regions (e.g., mosaic of n adjacent regions) is repeatable to increase a surface area of a substrate and a size of the cells grown thereon. The scalability of the repeatable unit provides flexibility in cell sheet size and allows cell sheets of larger surface area to be grown in comparison to cell sheets grown using conventional culture vessels such as a multi-well plate and roller bottles. In some embodiments, a cell culture substrate includes a surface comprising a plurality of regions corresponding to a plurality of patterned textures. In some embodiments, two or more of the regions have the same patterned texture. In some embodiments, a set of the plurality of regions are arranged periodically. In some embodiments, a set of the plurality of regions are arranged non-periodically. In some embodiments, the substrate has a substrate dimension and the patterned textures has a surface dimension. A ratio of the surface dimension to the substrate dimension is between about 0.0001:1 and about 0.1:1. The substrate dimension comprises one or more of width, length, depth, diameter, curvature, volume, and area of the substrate. The surface dimensions comprises one or more of width, length, depth, diameter, curvature, volume, and area of the surface. For example, a surface dimension of a set of radial grooves include one or more of radius of curvature of the grooves, depth of the grooves, width of the grooves, surface roughness, and the like. A substrate dimension of a planar circular substrate includes one or more of substrate thickness, substrate diameter, and the like.

One example of a scalable substrate includes a rectangular cell culture substrate having a set of three patterned textures arranged parallel to a longitudinal axis of the substrate. A first patterned texture may overlay a central region of the substrate that intersects the longitudinal axis. A second patterned texture is arranged parallel and adjacent to both sides of the first patterned texture. A third patterned texture is arranged parallel and adjacent to one side of the second patterned texture such that the third patterned texture is adjacent a longitudinal edge of the substrate. The set of patterned textures correspond to a set of density of surface features such that the density of surface features increases from the first patterned texture to the third patterned texture. Accordingly, the mechanical interaction between the surface and a population of cells increases in a direction perpendicular to the longitudinal axis.

II. Methods

Also described here are methods for culturing cells and manufacturing the cell culture substrates described herein. The methods described here allow for improved growth and adhesion of cells to a patterned texture cell culture substrate over a non-patterned texture cell culture substrate. In some embodiments, a non-patterned texture surface of a cell culture substrate is absent additional steps (e.g., shaping, or texturizing) to the surface post-substrate formation. For example, temporal characteristics of cell sheet release from the substrate are controlled by varying the characteristics of the patterned texture for a desired a cell type and/or application of the cell sheet. Additionally or alternatively, one or more cell substrates are arranged to increase a cell sheet surface area. The patterned textures correspond to one or more of a cell type, and growth and retention characteristics. A population of cells placed at one or more locations of a cell culture substrate are used to grow the cells into a cell sheet. The cell sheet may be detached from the substrate after the cells reach predetermined growth requirements such as size, maturity, and the like. A cell culture substrate manufacturing method forms one or more patterned textures on a surface of a cell culture substrate. The cell culture substrate used and manufactured as described herein is used in some embodiments in the absence of a scaffold structure.

Method of Culturing Tissue

Generally, the methods described here include contacting the cell culture substrate with a population of cells for a predetermined amount of time. Growth media (e.g., cell culture media) is delivered to the cells to promote one or more of cell growth, cell differentiation or maintenance of an undifferentiated cell state. The cells grown on the substrate may be detached as an unbroken (e.g., continuous) cell sheet and/or in predetermined sections. In some embodiments, the cells grown on the substrate are detached in a plurality of randomly sized sections. For example, a population of cells is grown on a surface of any of the cell culture substrates described herein. The cells mechanically interact and grow on the surface of the substrate to form a continuous cell sheet. In contrast to single cells or small groups of cells formed in a suspension, the methods described herein enable the production and consumption of a comestible meat product having a texture and consistency similar to a naturally produced meat product.

Although substantially planar cell culture substrates are described and illustrated herein, the cell culture substrates include non-planar substrates such as a curved substrate suitable for use in, for example, a bioreactor and/or roller bottle. In some embodiments, the cells are induced to contract and/or relax at a predetermined time and/or cell state to aid detachment of the cells from the substrate. In some embodiments, the patterned texture includes features that allow for one or more of directional cell contraction and relaxation. In some embodiments, the patterned texture is configured to aid one or more chemical, electrical, optical, fluidic, thermal, and mechanical-based detachment mechanisms.

Figure 6:
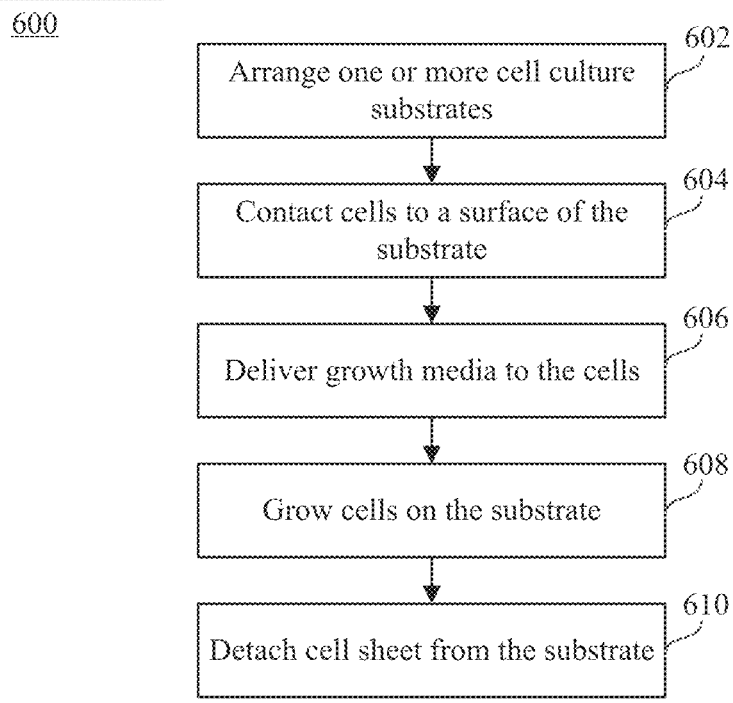
FIG. 6 is an illustrative flowchart of one method of culturing cells using one or more cell culture substrates comprising patterned textures, used to form a cell sheet.

FIG. 6 is a flowchart that generally describes a cell culture method (e.g., method of preparing a comestible meat product) using a cell culture substrate (600). The process (600) includes arranging one or more cell culture substrates. For example, one or more substrates are placed (e.g., disposed) into and/or integral with a suitable adherent culture vessel (602). As used herein, a culture vessel includes one or more of a bioreactor, well, petri dish, plate, flask, roller bottle, tank, box, fixed surface (e.g., floor, wall, table), combinations thereof, and the like. In some embodiments, a plurality of cell culture substrates are arranged in a parallel plate configuration. In some embodiments, one or more substrates may be disposed in a predetermined (e.g., fixed) arrangement within the culture vessel. Additionally or alternatively, one or more substrates may be free floating or disposed on a free floating structure configured to move freely within a culture vessel.

A population of cells are contacted onto a surface of one or more of the cell culture substrates (604). In some embodiments, the outer surfaces of the substrate may be wetted to prepare the substrate for cell seeding. For example, 0.5 mL of cell culture media is applied to the outer surface of the substrate. Cell culture media is optionally filled between the substrate and culture vessel and then removed. A set of cells are placed in each region of a substrate. For example, the cells are suspended in media and added dropwise over the substrate. As described herein, the cell culture substrate allows for improved growth and adhesion of the cells to the substrate comprising the patterned texture as compared to a surface not comprising the patterned texture.

Cell culture media is delivered to the population of cells (606) in any suitable manner. In some embodiments, cell culture media to the cells is delivered between adjacent cell culture substrates. The flow of cell culture media is controlled to prevent undesired release and/or shearing of cells from the substrate. For example, growth media may be applied in a continuous discontinuous manner in order to supply the cells (e.g., cell sheet, comestible meat product) with sufficient oxygen and nutrient to enable efficient metabolic exchange between the cells to the growth media.

The cells are grown on the substrate under a set of predetermined conditions (e.g., culture temperature, humidity, pH, dissolved oxygen) for a predetermined amount of time (606) to form a cell sheet. In some embodiments, cell culture media is added into a culture vessel such as a well plate or flask by one or more of a pipette and pump. For example, the cells may be configured to grow under a first set of conditions (e.g., first fluid flow rate of growth media for a first set of time) after the cells are contacted to a surface of the substrate. The cells may be configured to grow under a second set of conditions (e.g., a second fluid flow rate of growth media for a second set of time) after the first of time. The first fluid flow rate may be continuous while the second fluid flow rate may be discontinuous. A third fluid flow rate may be applied to the cell sheet in order to separate a cell sheet from the substrate on which it is adhered. In some embodiments, one or more of a pump, agitator, combinations thereof, and the like may be configured to deliver fluid to the cells.

In some embodiments, the size of the cell sheet may depend on the dimensions of the substrate. In some embodiments, the substrate may comprise one or more thicknesses.

The cell sheet may have a thickness (e.g., height) of at least about 1 μm. For example, the cell sheet has a thickness in a range of between about 1 μm and about 1 mm, between about 100 μm and about 1 mm, between about 200 μm and about 500 μm, and between about 300 μm and about 800 μm, including all values and sub-ranges in-between.

In some embodiments, the cell sheet is detached from the substrate at a predetermined time and/or cell state (610). In some embodiments, the cell sheet is detached as a substantially continuous, and/or whole, multi-layered piece. That is, the substrate enables improved intact and/or contemporaneous release of the cell sheet from the substrate as compared to substrates not comprising the patterned texture. The cell sheet need not be detached as a single piece, and may detach in predetermined portions rather than detach and break apart in an uncontrolled, arbitrary manner. In some embodiments, the cell sheet is detached in a set of separable sections. For example, the patterned texture is configured to allow a cell sheet grown on a cell culture substrate to be detached in a plurality of sections (e.g., 2 or more pieces).

In some embodiments, cell detachment from the substrate is performed using one or more mechanisms. For example, detachment of cells from a substrate may comprise one or more of spontaneous, chemical, electrical, optical, fluidic, thermal, and mechanical detachment by inducing contraction and/or relaxation of the cells. For example, one or more buffers or enzymatic solutions contact the cells to induce detachment from the substrate. In some embodiments, one or more of a volume and rate of fluid flow through a fluid channel used to deliver cell culture media are increased to detach the cell sheet. For example, fluid flow is increased between adjacent substrates in a parallel plate configuration to fluidically separate the cells sheet from the patterned texture surface. The fluid flow may be aligned to a direction of the patterned texture. As another example, fluid including air bubbles flows over the surface of a substrate, thereby creating turbulent flow configured to apply a shear force sufficient to detach a cell sheet from the substrate. In some embodiments, the fluid has a higher viscosity than the fluid used for cell culture media, which may increase the interfacial shear stress applied to the cell sheet, thereby facilitating cell sheet detachment.

Additionally or alternatively, a cell scraper is used to detach the cell sheet from the substrate. For example, the cell scraper separates the cell sheet in a direction parallel to the direction of the patterned texture. In some embodiments, the cell scraper is applied in a perpendicular direction or in a direction independent of the patterned texture. In some embodiments, a set of electrical impulses are applied to the cell sheet to stimulate cell contraction. In some embodiments, optical detachment includes a set of laser pulses applied to the cell sheet to stimulate intracellular Ca' release to induce contraction across an area of the cell sheet. Sufficient contractile force may aid detachment of the contracting cell sheet from the substrate.

Figure 7A:
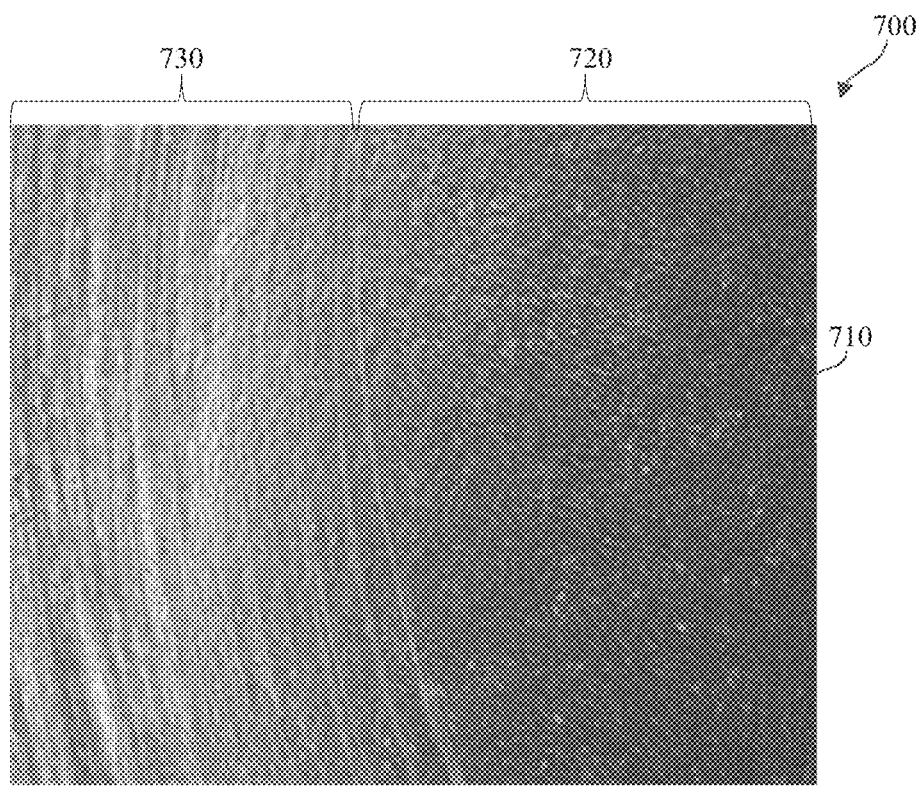
FIGS. 7A-7B are illustrative views of cell sheet growth on respective patterned texture regions and non-patterned surface regions of a cell culture substrate.
Figure 7B:
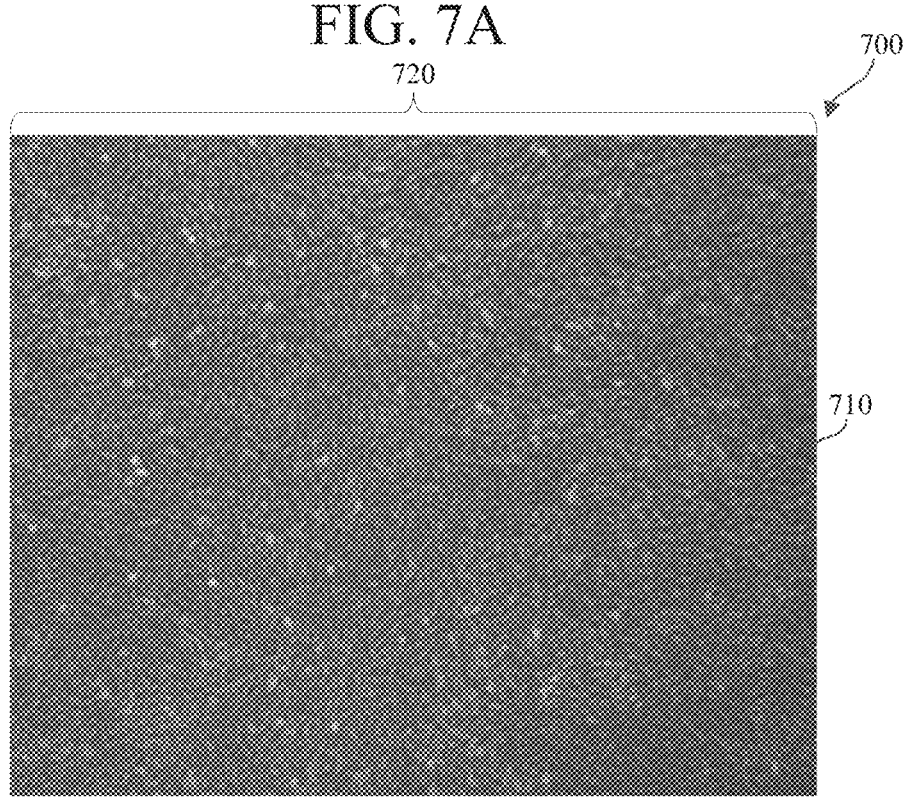

FIG. 7A is an image of cell sheet (710) growth on a surface of a cell culture substrate (700) having a non-patterned texture surface region (720) and a patterned texture surface region (730). FIG. 7B is an image of cell sheet (710) growth on the non-patterned texture surface region (720) of the cell culture substrate (700). The cell sheet (710) shown in FIGS. 7A and 7B are composed of fibroblasts and are grown continuously over the regions (720, 730). The patterned textures in FIGS. 7A and 7B are formed on the surface region (730) by applying 800 grit abrasive material (e.g., sandpaper, aluminum oxide paper, silicon carbide film) to the surface of the substrate (700). The patterned texture is formed in a circumferential direction over the region (730).

Figure 8A:
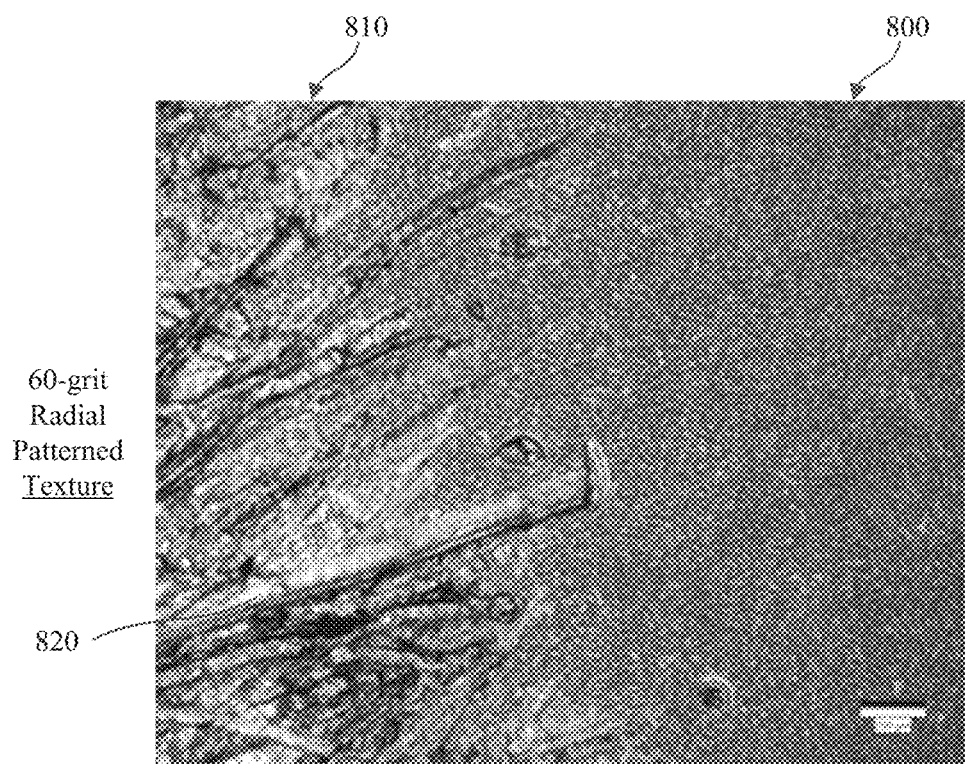
FIG. 8A is an illustrative view of fibroblasts grown on a radially patterned texture surface region of a cell culture substrate.
Figure 8B:
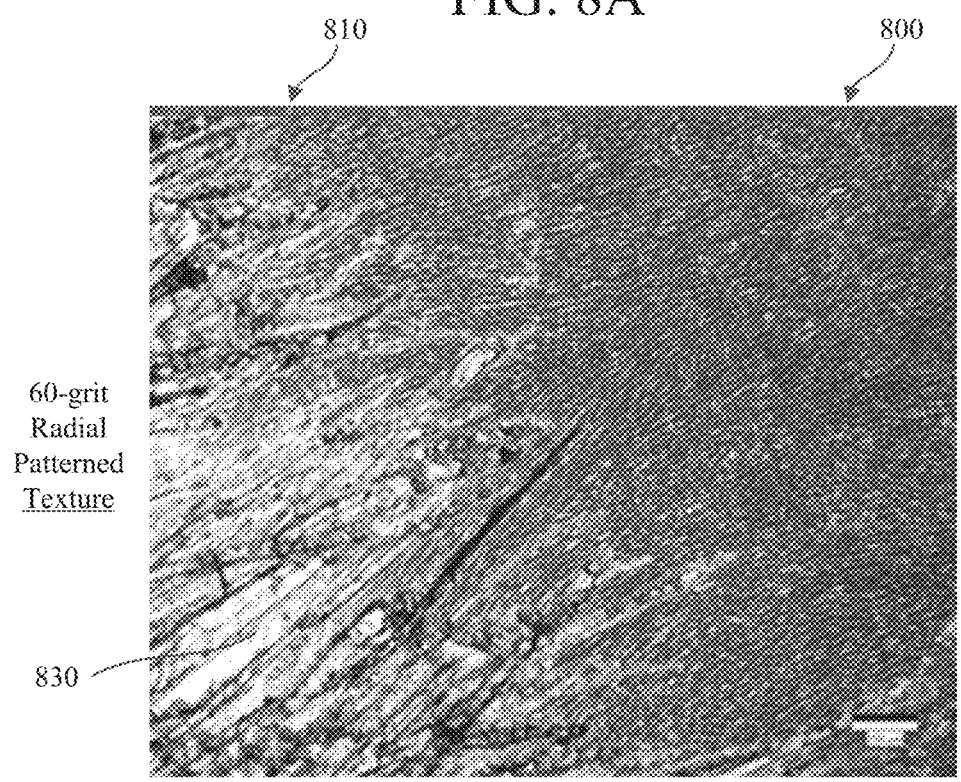
FIG. 8B is another illustrative view of fibroblasts and cardiac cells grown on a radially patterned texture surface region of a cell culture substrate.

FIG. 8A is an image of fibroblast (820) growth on a radial patterned texture surface region (810) of a cell culture substrate (800). FIG. 8B is an image of fibroblast (830) growth on a radial patterned texture surface region (810) of a cell culture substrate (800). The cell sheets (820, 830) shown in FIGS. 8A and 8B are grown continuously over the patterned texture regions (810). The patterned textures are formed in FIGS. 8A and 8B by applying 60 grit abrasive material (e.g., sandpaper, aluminum oxide paper, silicon carbide film) to the surface of the substrate (800) in a radial direction. In some embodiments, as the fibroblasts mature and elongate, they may tend to align with the direction of a patterned texture.

Method of Manufacturing Cell Culture Substrates

Also described herein are methods of manufacturing the described cell culture substrates. In some methods, one or more patterned textures are formed on a surface of a substrate by one or more of additive and subtractive manufacturing techniques. For example, a patterned texture is formed by one or more of adding, removing, and restructuring material on the surface of a cell culture substrate by one or more mechanical, chemical, and electromagnetic techniques.

Generally, a method of manufacturing a cell culture substrate includes forming (e.g. introducing) one or more patterned textures on the cell culture substrate. The substrate comprises a plurality of regions corresponding to one or more of the patterned textures. In some embodiments, forming the plurality of patterned textures includes one or more of additive and subtractive manufacturing. In some of these embodiments, forming the plurality of patterned textures includes one or more of machining, cutting, milling, abrasion, etching, engraving, embossing, scratching, scoring, casting, water discharge, chemical etching, laser ablation, electron beam lithography, sputter coating, vapor-phase deposition, printing, adhesive bonding, and welding. For example, one or more of a rotary tool, blade, die cutter, and laser energy cuts and/or engrave a surface of the substrate. The rotary tool is used, for example, in a milling process.

Figure 11:
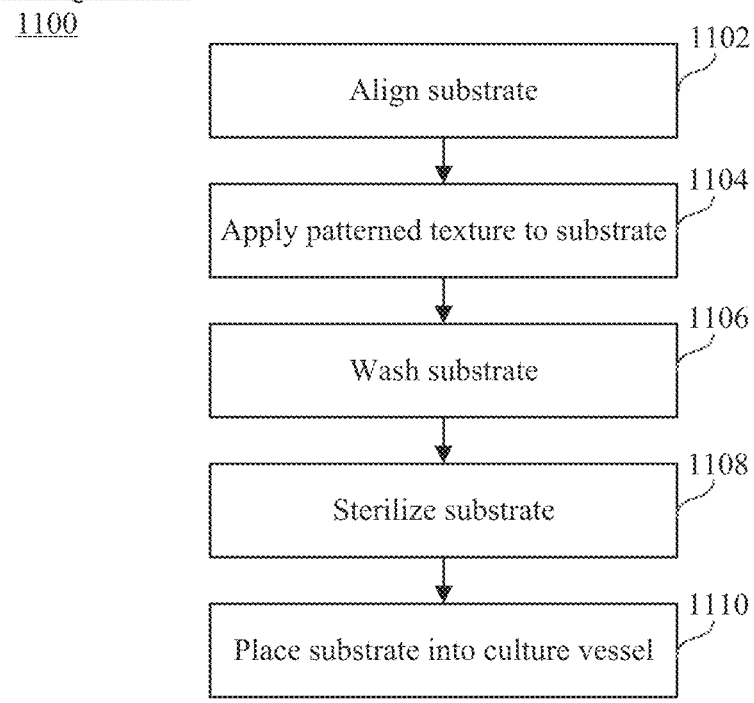
FIG. 11 is an illustrative flowchart of an exemplary method of manufacturing a cell culture substrate comprising a patterned texture.

In some embodiments, a patterned texture is manufactured to comprise one or more channels, recesses, and protrusions. FIG. 11 is a flowchart that generally describes an illustrative method (1100) of manufacturing a patterned textured cell culture substrate. One or more manufacturing techniques may be used on the surface to enhance one or more of growth, adhesion, retention, and release characteristics. The process (1100) includes aligning one or more cell culture substrates to a manufacturing apparatus (e.g., die cutter, laser) (1102) such that one or more predetermined patterned textures are applied to one or more predetermined portions of the substrate. In this illustrative process, a PCTFE substrate of about 200 μm thickness substrate is aligned to a die cutter. A predetermined patterned texture is applied to the substrate (1104) using the manufacturing apparatus. For example, the die cutter etches the surface of the substrate with grooves of about 40 μm. The substrate is washed (1106) and then sterilized (1108). For example, the substrate is removed from the die cutter and washed to remove etching debris remaining on the surface of the substrate. In some embodiments, the substrate is washed in a sonic bath using a cleansing agent (e.g., 1% liquinox). The substrate is then sterilized using, for example, an autoclave. Additional surface processing steps may be performed. For example, in some embodiments the surface of the substrate is washed/sterilized and a biocompatible coating is applied over the surface of the substrate. A coating can be applied over the surface of the substrate either before, or after the patterned texture is applied. A patterned texture may increase the surface area of a substrate so as to improve a precoating process under wet or dry conditions and increase retention time of the coating on the substrate.

The sterile cell culture substrate is placed into the culture vessel (1110). The sterile cell culture substrate may be subsequently used in a cell culture method as described in more detail with respect to FIG. 6. As described herein, the cell culture substrate allows for improved growth and adhesion of the cells to the substrate comprising the patterned texture as compared to a surface not comprising the patterned texture.

In some embodiments, the surfaces having the patterned textures described herein are manufactured to comprise a plurality of channels each having a depth of between about 0.1 μm and about 300 μm, between about 0.1 μm and about 250 μm, between about 0.1 μm and about 150 μm, between about 0.1 µm and about 100 µm, between about 1 µm and about 50 µm, and between about 20 µm and about 80 µm, including all values and sub-ranges in-between. The plurality of channels as manufactured may have a width of between about 1 µm and about 5 mm, between about 1 µm and about 3 mm, between about 1 µm and about 2 mm, and between about 1 µm and about 1 mm, including all values and sub-ranges in-between. Adjacent channels may be introduced and be separated from each other by at least about 5 µm, between about 5 µm and about 5 cm, between about 5 µm and about 3 cm, between about 25 µm and about 100 µm, between about 100 µm and about 500 µm, between about 5 µm and about 500 µm, and between about 500 µm and about 3 cm, including all values and sub-ranges in-between. Generally, the cell culture substrates into which the textures are introduced has a thickness of at least about 10 µm. In some embodiments, a cell culture substrate has a thickness of between about 10 µm and about 10 cm, between about 10 µm and about 1 mm, between about 5 mm and about 2 cm, and between about 1 cm and 5 cm, including all values and sub-ranges in-between.

In some embodiments, the plurality of regions are introduced to be arranged periodically. In some embodiments, the plurality of regions are arranged non-periodically. In some embodiments, the substrate are placed (e.g., disposed) into and/or integral with a culture vessel. In some embodiments, the substrates are arranged adjacent to at least one other cell culture substrate. In some embodiments, the substrates are arranged in a three-dimensional lattice.

In some embodiments, the patterned texture comprises a predetermined direction. The patterned texture has one or more directions comprising circumferential, radial, cross-hatched, random, linear, curved, ovoid, ellipsoid, sinusoidal, non-linear (e.g., zigzag), combinations thereof, and the like. For example, a cross-hatched direction is defined by a set of intersecting lines (e.g., parallel lines, curved lines). In some embodiments, the patterned texture comprises a random spatial distribution pattern within one or more regions of a surface.

In some embodiments, the ratio of a first surface area having a patterned texture to a second surface area having a non-patterned texture is between at least about 0.0001:1 and up to about 1:0 (corresponding to a surface completely covered by a patterned texture), between about 0.1:1 and about 1:1, between about 1:1 and about 100:1, and between about 10:1 and about 1000:1, including all values and sub-ranges in-between. In some embodiments, the spatial distribution of one or more patterned textures across a plurality of regions of the substrate is symmetric, asymmetric, periodic, non-periodic, random, combinations thereof, and the like. Illustrative manufacturing techniques are described in more detail herein.

Abrasive Material

Cell culture substrates formed by abrasion are scalable and applicable to nearly all substrate materials. Abrasion is particularly effective for generating broad parallel patterned textures. In some embodiments, one or more patterned textures are formed on a cell culture substrate using an abrasive material having a grit of between about 24 grit and about 1500 grit, including all values and sub-ranges in-between. The abrasive material is composed of aluminum oxide, silicon carbide, emery, chromium(III) oxide, combinations thereof, and the like. Coarser abrasive material may facilitate stronger cell adhesion but hinder cell release. The abrasive material may be moved relative to the substrate in a direction of the patterned texture (e.g., linearly, radially, circumferentially). The abrasive material is applied to the surface of the substrate between about 1 and about 5-2000 times (e.g., revolutions) and then removed from the surface. The substrate is washed to remove debris and sterilized to complete the manufacturing process. For example, as described herein, the cell culture substrates in FIGS. 1A-1B, 2A-2C, 7A-7B, and 8A-8B are formed using abrasion.

Laser

Cell culture substrates formed by a laser may generate uniform patterned textures on a surface of a substrate. In some embodiments, one or more patterned textures are formed on a cell culture substrate using a laser to etch, engrave, mark, cut, drill, and/or modify a surface of the substrate. For example, the laser ablates material from the surface of the substrate. In some embodiments, a photomask is used in forming the patterned texture. Laser manufacturing is useful in providing a uniform surface and may form complex patterns with high accuracy and precision. For example, as described herein, the cell culture substrates in FIGS. 4A-4B are formed using laser etching.

Die Cutter

Cell culture substrates formed by a die cutter may generate repeatable and consistent patterned textures on substrate surfaces. In some embodiments, one or more patterned textures are formed on a cell culture substrate using a die cutter. One or more dies may include a set of blades. The die may include one or more patterned textures. For example, as described herein, the cell culture substrates in FIGS. 3A-3C are formed using die-cutting.

EXAMPLES

Example 1: Illustrative Patterned Textures

As described herein, the cell culture substrates have a patterned texture that allows for improved growth, adhesion, and retention of cells on the substrate, and/or improved release of cells from the substrate, as compared to other substrates and surfaces not comprising a patterned texture.

Table 1 lists a set of cell culture substrates and illustrative patterned texture surface dimensions in microns, referring further to exemplary drawings. The physical dimensions of the surfaces were measured using non-contact surface profilometry.

TABLE 1

| Referring to FIG. | Substrate | Manufacturing technique | Patterned texture direction | Depth (µm) | Width (µm) | Gap (µm) |
| --- | --- | --- | --- | --- | --- | --- |
| 4B | Stainless steel | Laser etch | Radial | 4 | 50 | 80 |
| 4A | Thermoplastic—PEI | Abrasive—800 grit | Radial | 0.5 | 2-10 | ~30 |
|  | Thermoplastic—PEI | Abrasive—60 grit | Radial | 40 | 60 | 800 |
|  | Thermoplastic—PCTFE | Die cut | Linear | 40 | 60 | 50 |
| 3A | Thermoplastic—PCTFE | Die cut | Radial | 40 | 60 | 50-60 |
|  | Thermoplastic—PCTFE | Die cut | Radial | 40 | 60-80 | 60 |

TABLE 1-continued

| Referring to FIG. | Substrate | Manufacturing technique | Patterned texture direction | Depth (μm) | Width (μm) | Gap (μm) |
|---|---|---|---|---|---|---|
|  | Thermoplastic—PCTFE | Abrasive—800 grit | Radial | ~1 | 10-20 | 20 |
|  | Thermoplastic—PCTFE | Abrasive—800 grit | Spots | 1-2 | 10 | 10-15 |
| 10D | Thermoplastic—PCTFE | Abrasive—800 grit | Linear and spots | 1 | 5-10 | 10 |

Example 2: Retention of Cell Sheets Under Varying Growth Conditions

For each of the substrates shown in FIGS. 12A-17, a population of cells were grown on respective substrates.

The cells mechanically interacted with the patterned textures introduced onto the substrates, and resulted in the increase adhesion of cells to the substrate for a longer amount of time compared to a substrate (e.g., Tissue Culture treated Polystyrene Substrate (TCPS)) not having a patterned texture surface while maintaining health and viability of the cells (Table 2). The cell culture substrates shown in FIGS. 12A-17 may also be used in scalable parallel-plate bioreactors.

Table 2 (below) lists a set of cell culture substrates (corresponding to FIGS. 12A-17) and days of retention on the substrate for different cell lines and growth conditions (e.g., static, flow). In particular, cell line A was a poultry fibroblast line and cell line B was a co-culture of poultry fibroblasts and myoblasts. Each of the cell lines were cultured in an incubator at a temperature between 37° C. and 40° C. with 5% $CO_2$. For example, culture media was passed over the surface of the cells grown on the cell culture substrates using a peristaltic pump. The #3 Brushed Stainless Steel is composed of stainless steel (e.g., 304 or 316 stainless steel) with unidirectional grain with 60-80 grit finish across the entire surface.

TABLE 2

Days of Retention on Cell Culture Substrate

|  | Static with Cell Line A | Static with Cell Line B | Flow with Cell Line B |
|---|---|---|---|
| #3 Brushed Stainless Steel | 9 | 14 | 14 |
| Cell Culture Substrate (1200) | 14* | 14* | 12 |
| Cell Culture Substrate (1300) | 7 | N/A | N/A |
| Cell Culture Substrate (1400) | 14* | 14* | 14* |
| Cell Culture Substrate (1500) | 14* | 14* | 11 |
| Cell Culture Substrate (1600) | 7 | N/A | N/A |
| Cell Culture Substrate (1700) | 14 | 14 | 14 |
| Tissue Cultured treated Polystyrene Substrate (TCPS) | 7 | N/A | N/A |

*Cells detached from cell culture substrate as a single intact cell sheet

Example 3: Cell Sheet Retention

Figure 9A:
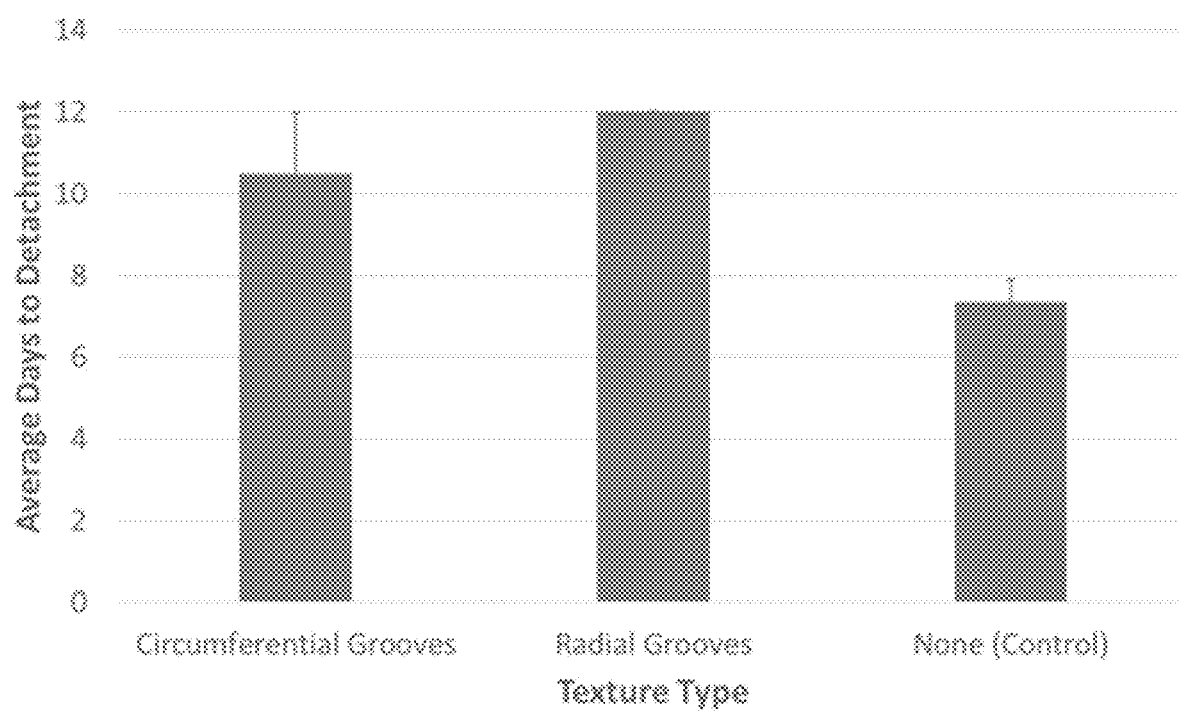
FIG. 9A is an illustrative comparison of cell sheet retention grown on an exemplary patterned texture cell culture substrates and non-patterned texture cell culture substrates.
Figure 9B:
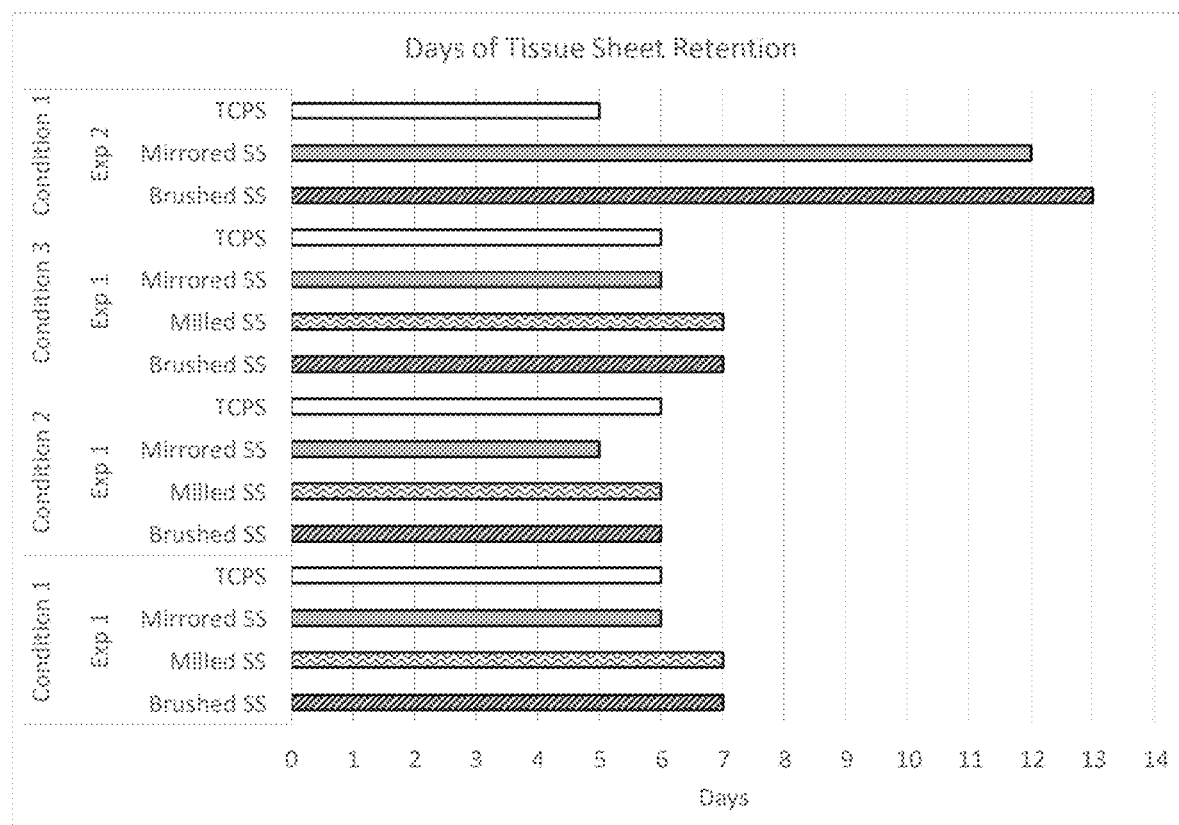
FIG. 9B is an illustrative comparison of cell sheet retention grown on an exemplary patterned texture cell culture substrates and non-patterned texture cell culture substrates under different conditions.

FIG. 9A is an illustrative comparison of cell sheet retention of patterned texture cell culture substrates to non-patterned texture cell culture substrates. As seen in FIG. 9A, cell sheet retention was improved in patterned texture substrates over control substrates having no patterned textures. The cell culture substrates used in FIG. 9A were composed of PCTFE with circumferential or radial textures formed using 60 grit or 800 grit abrasive material. The cells included cardiac and dermal fibroblast cell types. It should be noted that the cell sheets attached to the patterned texture substrates in FIG. 9A were detached at twelve days. However, cell sheet growth and retention has been demonstrated for at least about 30 days. FIG. 9B is another illustrative comparison of cell sheet retention of textured cell culture substrates to non-textured cell culture substrates. Cells cultures were grown under different experimental conditions (e.g., conditions 1, 2, 3) and experiments (e.g., experiments 1, 2). Cell cultures were grown under different media between Condition 1 and Conditions 2 and 3. The method of culturing cells prior to the experiment were different between Condition 3 and Conditions 1 and 2. Experiment 1 used a cell culture of chicken fibroblasts and Experiment 2 used a mixed cell culture of chicken fibroblasts and myoblasts. As seen in FIG. 9B, cell cultures grown on the textured surfaces provided increased cell retention to the substrate. For example, brushed stained steel (e.g., brushed SS) and milled stainless steel (e.g., milled SS) substrates have more texture than a mirrored stainless steel (e.g., mirrored SS) and Tissue Culture treated Polystyrene (TCPS) substrates.

Example 4: Cell Sheet Retention

Figure 18A:
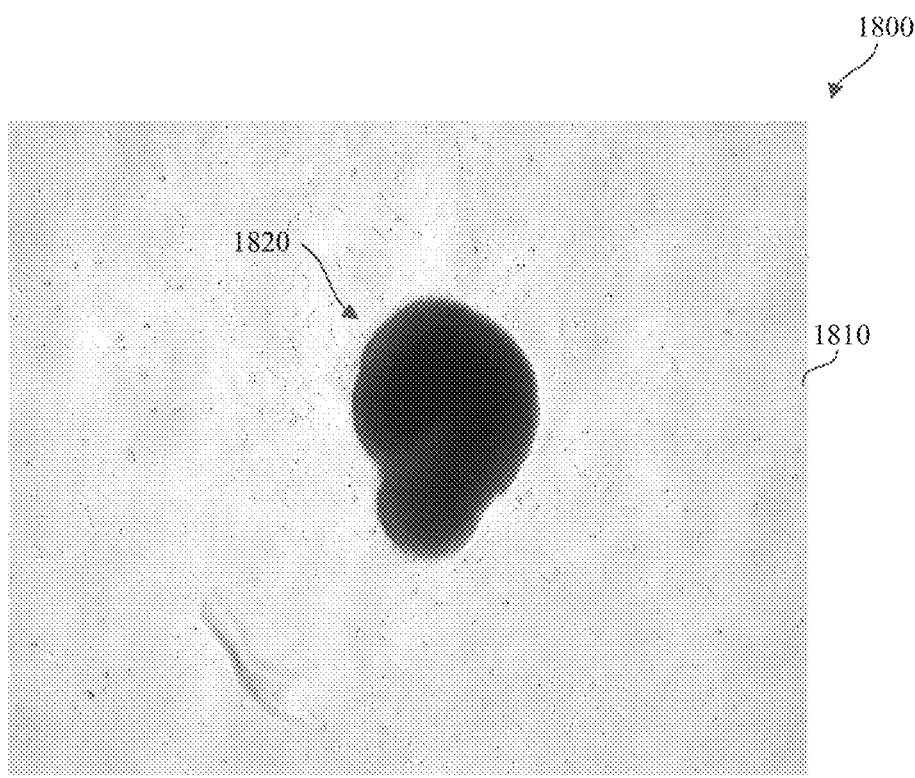
FIGS. 18A-18D are illustrative views of cell sheet growth on respective non-patterned texture regions and patterned texture regions of a cell culture substrate.
Figure 18B:
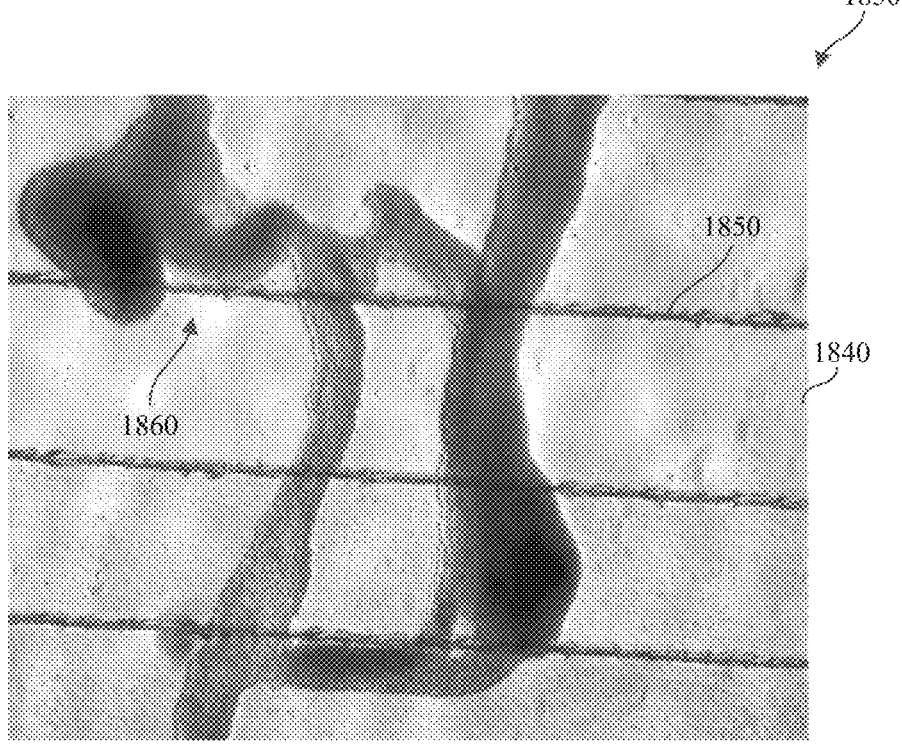
Figure 18C:
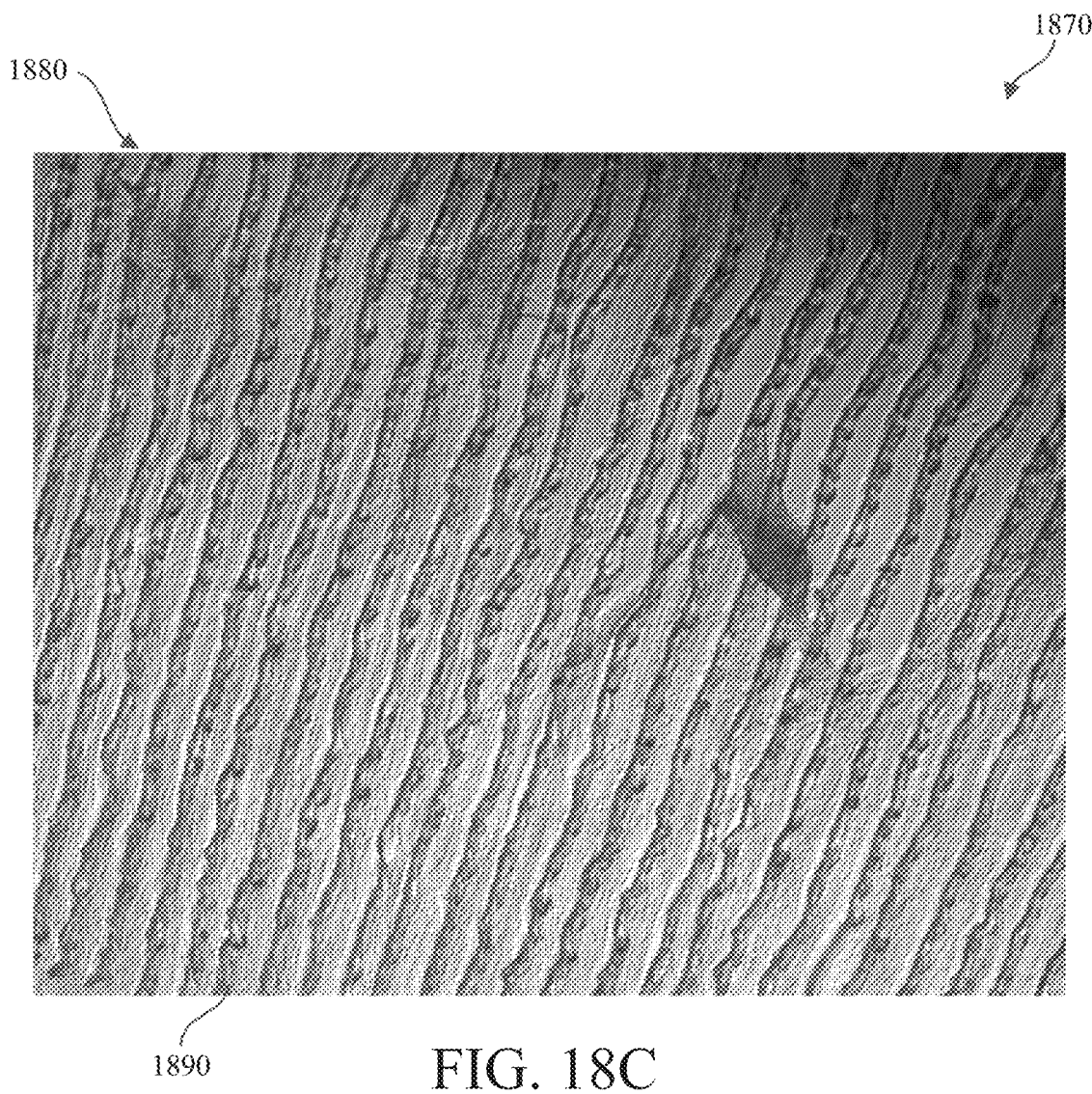
Figure 18D:
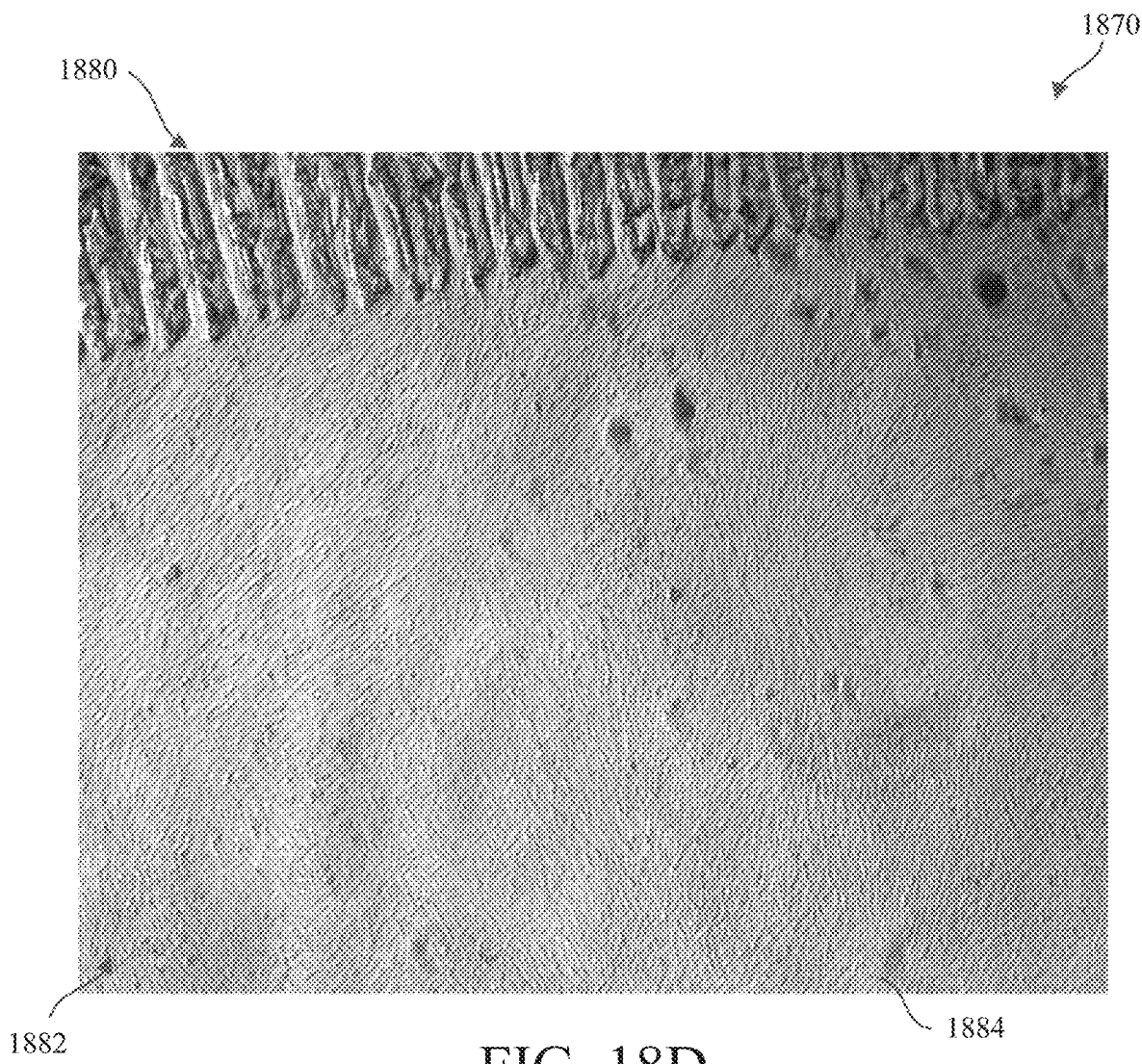

FIGS. 18A-18D are images of cell growth of avian cells on respective non-patterned texture regions and patterned texture regions of a cell culture substrate after four days of cell culture. In FIGS. 18A-18D, the substrates (1800, 1830, 1870) were sterilized with ethanol and rinsed with phosphate buffered saline (PBS) prior to cell seeding. A population of cells were seeded onto each substrate with growth media (e.g., FPM-38) under incubation conditions of about 39° C., about 5% $CO_2$ and about 95% humidity. Growth media was exchanged after day three and day four of culturing. FIG. 18A is an image of a cell culture substrate (1800) composed of polychlorotrifluoroethylene (PCTFE) having a non-patterned texture surface (1810) (e.g., naïve smooth, absent surface modification). Without a patterned texture surface, the cells (1820) agglomerated into a nodule that has separated from the substrate (1800) where the nodule is free-floating.

FIG. 18B is an image of a cell culture substrate (1830) composed of polychlorotrifluoroethylene (PCTFE) having a patterned texture surface (1840) comprising a set of parallel linear channels (1850) spaced apart from each other by about 1 mm. In FIG. 18B, tissue (1860) growth was not well retained to the substrate (1830). For example, the darker portions of the tissue (1860) correspond to free-floating cells separated from the substrate (1830).

FIG. 18C is an image of a cell culture substrate (1870) composed of polychlorotrifluoroethylene (PCTFE) having a patterned texture surface (1880) comprising a set of parallel linear channels (1890) spaced apart from each other by about 65 µm. In FIG. 18C, tissue sheets (1890) were generally retained across the entire substrate (1870). The entire substrate surface need not comprise the patterned texture surface (1880) as shown in FIG. 18D. In some embodiments, for example, a continuous cell sheet may be formed and retained on a substrate comprising a periodic pattern of a non-patterned texture surface (1890) between respective patterned texture surfaces (1880). FIG. 18D is an image of a cell culture substrate (1870) composed of polychlorotrifluoroethylene (PCTFE) having a patterned texture surface (1880) comprising a set of parallel linear channels spaced apart from each other by about 65 µm and adjacent to a non-patterned texture surface (1882). The substrate may comprise a diameter of, for example, at least 3 cm where at least an edge region of the substrate comprises the patterned texture surface (1880). A continuous cell sheet (1884) was grown and retained across the substrate (1870) after four days of growth.

Example 5: Cell Sheet Adhesion and Alignment

Figure 19:
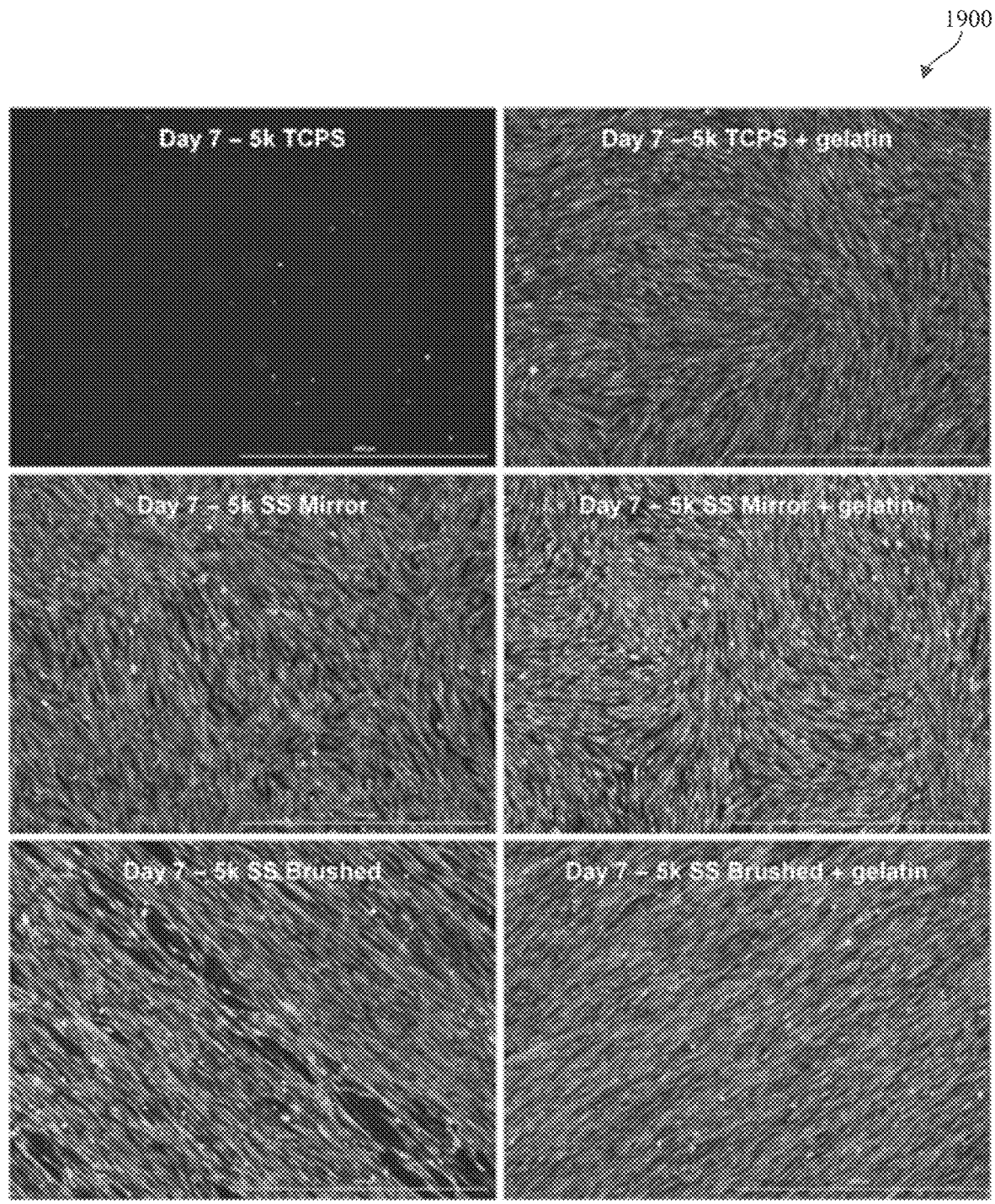
FIG. 19 are illustrative views of cell sheet growth on patterned texture regions of cell culture substrates.

FIG. 19 depicts a set of images (1900) of cell sheet growth on a set cell culture substrates (700) each over about seven days. For example, 9 billion cells were grown on each substrate over seven days. In particular, calcein staining of the cytoplasm of the cells shows the overall morphologoy of the cell bodies. A Hoescht counterstain of the nuclei allows verification that calcein stain identifies individual cells. The substrates included Tissue Culture treated Polystyrene (TCPS) substrates, mirrored stainless steel, brushed stained steel, and variations including a gelatin coating. As shown in FIG. 19, cells may grow on a substrate and align (e.g., conform) to a patterned texture of the substrate. For example, surface integrin interactions may transduce signaling to cell nuclei by, for example, cytoskeletal mechanotransduction, resulting in the activation and inhibition of active domains in the nucleus that direct the direction of cell growth.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the substrates described herein may be used in any combination, and the methods described herein may comprise all or a portion of the elements described herein. The description of certain elements or characteristics with respect to a specific figure are not intended to be limiting or nor should they be interpreted to suggest that the element cannot be used in combination with any of the other described elements.

In addition, any combination of two or more such features, structure, systems, articles, materials, kits, steps and/or methods, disclosed herein, if such features, structure, systems, articles, materials, kits, steps and/or methods are not mutually inconsistent, is included within the inventive scope of the present disclosure. Moreover, some embodiments disclosed herein may be distinguishable from the prior art for specifically lacking one or more features/elements/functionality found in a reference or combination of references (i.e., claims directed to such embodiments may include negative limitations).

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

What is claimed is:

1. A method of preparing a comestible meat product, comprising:
   applying a plurality of non-human cells comprising at least one muscle-derived cell and one or more additional cells, at any state of differentiation, from at least one of myoblasts, mesoangioblasts, myofibroblasts, myotubes, mesenchymal stem cells, hepatocytes, fibroblasts, pericytes, adipocytes, adipose tissue, epithelial, chondrocytes, osteoblasts, osteoclasts, pluripotent cells, somatic stem cells, endothelial cells, epithelial tissue, vascular endothelium, or contractile cells to a solid patterned texture substrate comprising a first patterned texture region and a second patterned texture region, wherein a texture of the first patterned texture region differs from a texture of the second patterned texture region;
   growing the plurality of non-human cells on the solid patterned texture substrate to form the comestible meat product; and
   separating the comestible meat product from the solid patterned texture substrate.

2. The method of claim 1, wherein separating the comestible meat product from the solid patterned texture substrate comprises separating the comestible meat product from the solid patterned texture substrate in sections.

3. The method of claim 2, wherein separating the comestible meat product from the solid patterned texture substrate in sections comprises separating randomly sized sections of the comestible meat product from the solid patterned texture substrate.

4. The method of claim 1, wherein separating the comestible meat product from the solid patterned texture substrate comprises separating the comestible meat product from the solid patterned texture substrate as one or more cell sheets.

5. The method of claim 4, wherein separating the comestible meat product from the solid patterned texture substrate as one or more cell sheets comprises separating a first cell sheet section from the first patterned texture region and separating a second cell sheet section from the second patterned texture region.

6. The method of claim 4, wherein separating the comestible meat product from the solid patterned texture substrate as one or more cell sheets comprises separating a multilayered cell sheet from the solid patterned texture substrate.

7. The method of claim 1, further comprising directing a cell culture medium over the solid patterned texture substrate in a direction perpendicular to one or more of the first patterned texture region or the second patterned texture region.

8. The method of claim 1, wherein the first patterned texture region is less adherent than the second patterned texture region.

9. The method of claim 8, wherein separating the comestible meat product from the solid patterned texture substrate comprises directing a fluid across the first patterned texture region and then across the second patterned texture region.

10. A method of preparing a comestible meat product, the method comprising:
applying a plurality of non-human cells comprising at least one muscle-derived cell and one or more additional cells, at any state of differentiation, from at least one of myoblasts, mesoangioblasts, myofibroblasts, myotubes, mesenchymal stem cells, hepatocytes, fibroblasts, pericytes, adipocytes, adipose tissue, epithelial, chondrocytes, osteoblasts, osteoclasts, pluripotent cells, somatic stem cells, endothelial cells, epithelial tissue, vascular endothelium, or contractile cells to at least one patterned texture substrate; and
growing the plurality of non-human cells on the at least one patterned texture substrate to form a comestible meat product, wherein an arrangement of patterned textures of the at least one patterned texture substrate inhibits release of the plurality of non-human cells for a predetermined amount of time or until the plurality of non-human cells achieve a predetermined cell state.

11. The method of claim 10, further comprising separating the comestible meat product from the at least one patterned texture substrate.

12. The method of claim 11, wherein separating the comestible meat product from the at least one patterned texture substrate comprises directing a fluid over the at least one patterned texture substrate to detach the comestible meat product from the at least one patterned texture substrate.

13. The method of claim 10, further comprising positioning a plurality of patterned texture substrates in a bioreactor in a parallel plate configuration, wherein the at least one patterned texture substrate is one of the plurality of patterned texture substrates.

14. The method of claim 13, further comprising delivering a cell culture media between patterned texture substrates of the plurality of patterned texture substrates.

15. The method of claim 10, further comprising directing a cell culture medium over the at least one patterned texture substrate to generate a fluid flow pattern.

16. The method of claim 15, wherein the fluid flow pattern generates micro-turbulences that increase metabolic exchanges.

17. A method of preparing a comestible meat product, the method comprising:
applying a plurality of non-human cells comprising at least one muscle-derived cell and one or more additional cells, at any state of differentiation, from at least one of myoblasts, mesoangioblasts, myofibroblasts, myotubes, mesenchymal stem cells, hepatocytes, fibroblasts, pericytes, adipocytes, adipose tissue, epithelial, chondrocytes, osteoblasts, osteoclasts, pluripotent cells, somatic stem cells, endothelial cells, epithelial tissue, vascular endothelium, or contractile cells to at least one cell-adherent patterned texture of a patterned texture substrate;
growing the plurality of non-human cells applied to the patterned texture substrate to form a comestible meat product; and
separating the comestible meat product from the patterned texture substrate by directing fluid in a direction aligned with an adhesion gradient of adhesion quality between the comestible meat product and the patterned texture substrate.

18. The method of claim 17, wherein the adhesion gradient of adhesion quality between the comestible meat product and the patterned texture substrate is created by a gradient of textures on the patterned texture substrate that transition from less adherent to more adherent.

19. The method of claim 17, wherein the patterned texture substrate comprises a first side having protrusions that provide texture and a second opposing side lacking protrusions.

20. The method of claim 17, wherein separating the comestible meat product from the patterned texture substrate by directing fluid comprises delivering the fluid perpendicularly to a texture pattern of the patterned texture substrate.

* * * * *